United States Patent [19]

Chandrakumar et al.

[11] Patent Number: 5,395,932

[45] Date of Patent: Mar. 7, 1995

[54] 2,3-,4-,5-,6-,7-,8-,9- AND/OR 10-SUBSTITUTED DIBENZOXAZEPINE COMPOUNDS, PHARMACEUTICAL COMPOSITIONS AND METHODS OF USE

[75] Inventors: Nizal S. Chandrakumar, Vernon Hills; Timothy J. Hagen, Gurnee; Barnett S. Pitzele, Skokie; Sofya Tsymbalov, Des Plaines; E. Ann Hallinan, Evanston, all of Ill.

[73] Assignee: G. D. Searle & Co., Chicago, Ill.

[21] Appl. No.: 56,704

[22] Filed: Apr. 30, 1993

[51] Int. Cl.[6] .................. C07D 413/14; C07D 417/14; A61K 31/55

[52] U.S. Cl. ................................ 540/547; 548/333.5; 548/342.5

[58] Field of Search ........................ 540/547; 514/211

[56] References Cited

U.S. PATENT DOCUMENTS

| | | | |
|---|---|---|---|
| 2,852,528 | 9/1958 | Hoffmann | 260/327 |
| 3,210,372 | 10/1965 | Werner | 260/309.6 |
| 3,357,998 | 12/1967 | Cusic | 260/333 |
| 3,534,019 | 10/1970 | Coyne | 260/239 |
| 3,624,104 | 11/1971 | Cusic | 260/333 |
| 3,917,649 | 11/1975 | Mueller | 260/333 |
| 3,989,719 | 11/1976 | Mueller | 260/333 |
| 3,992,375 | 11/1976 | Mueller | 260/240 |
| 4,045,442 | 8/1977 | Mueller | 260/293 |
| 4,125,532 | 11/1978 | Mueller | 260/244 |
| 4,170,593 | 10/1979 | Mueller | 260/243.3 |

(List continued on next page.)

FOREIGN PATENT DOCUMENTS 0012385 6/1980 European Pat. Off. ... C09D 267/20
0193822 9/1986 European Pat. Off. ... C07D 267/20

(List continued on next page.)

OTHER PUBLICATIONS

07/778,074 U.S. (Application) (2668)–Hagen Nov. 5, 1991.

(List continued on next page.)

*Primary Examiner*—Emily Bernhardt
*Assistant Examiner*—Philip I. Datlow
*Attorney, Agent, or Firm*—Roberta L. Hastreiter; Roger A. Williams

[57] ABSTRACT

The present invention provides substituted dibenzoxazepine compounds of Formula I:

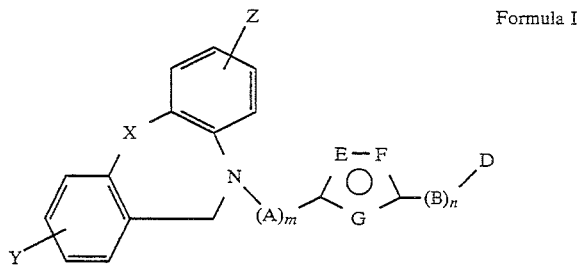

Formula I wherein X is oxygen, sulfur

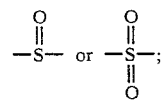

A is —$CH_2$— or

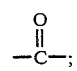

E and F may be —CH, oxygen, nitrogen or sulfur, and may not be the same; G is oxygen, nitrogen or sulfur; with the proviso that when G is oxygen or sulfur, one of E or F is nitrogen, which are useful as analgesic agents for the treatment of pain, and as prostaglandin-$E_2$ antagonists for the treatment of prostaglandin-$E_2$ mediated diseases, pharmaceutical compositions comprising a therapeutically-effective amount of a compound of Formula I in combination with a pharmaceutically-acceptable carrier, a method for eliminating or ameliorating pain in an animal, and a method for treating prostaglandin-$E_2$ mediated diseases in an animal, comprising administering a therapeutically-effective amount of a compound of Formula I to the animal.

6 Claims, No Drawings

U.S. PATENT DOCUMENTS

| | | | |
|---|---|---|---|
| 4,290,953 | 9/1981 | Koizumi | 260/333 |
| 4,379,150 | 4/1983 | Ito | 424/244 |
| 4,559,336 | 12/1985 | Mueller | 514/211 |
| 4,559,337 | 12/1985 | Mueller | 514/211 |
| 4,614,617 | 9/1986 | Mueller | 540/547 |
| 4,681,939 | 7/1987 | Mueller | 540/547 |
| 4,704,386 | 11/1987 | Mueller | 514/211 |
| 5,180,720 | 1/1993 | Husa | 514/211 |
| 5,182,272 | 1/1993 | Hallinan | 514/80 |
| 5,212,169 | 5/1983 | Huse et al. | 514/211 |
| 5,225,417 | 7/1993 | Dappen et al. | 514/279 |
| 5,281,590 | 1/1994 | Husa et al. | 514/211 |
| 5,283,240 | 2/1994 | Hallinan et al. | 514/80 |
| 5,288,719 | 2/1994 | Husa et al. | 514/211 |
| 5,288,719 | 2/1994 | Husa et al. | 514/211 |
| 5,304,644 | 4/1994 | Husa et al. | 540/547 |

FOREIGN PATENT DOCUMENTS

| | | | |
|---|---|---|---|
| 0218077 | 4/1987 | European Pat. Off. | C07D 267/20 |
| 0480641A1 | 4/1992 | European Pat. Off. | C07D 223/20 |
| 0534667 | 3/1993 | European Pat. Off. | C07D 417/06 |
| 6700603 | 7/1967 | Netherlands | |
| 1170322 | 11/1969 | United Kingdom | C07D 87/54 |
| 1331892 | 9/1973 | United Kingdom | |
| 1522003 | 8/1978 | United Kingdom | C071/267/20 |
| US92/06584 | of 0000 | WIPO | |
| WO92/19617 | 11/1992 | WIPO | C07D 413/12 |
| WO93/09104 | 5/1993 | WIPO | C07D 267/20 |

OTHER PUBLICATIONS

07/813,316 U.S. (Application) (2690)–Hagen Dec. 20, 1991.

07/869,563 U.S. (Application) (2603)–Husa Apr. 15, 1992.

08/006,858 U.S. (Application) (2667/1)–Husa Jan. 13, 1993.

08/021,694 U.S. (Application) (2687/1)–Dappen Feb. 24, 1993.

V. P. Arya, et al. "Antihypertensive Agents: Part IV"–Synthesis & Hypotensive Activity of Certain 2-Substituted 4,5-Dihydromidazoles, *Indian Journal of Chemistry*, 15B, 148–153 Feb. (1977)–India.

A. Bennett, et al. "Antagonism of Prostanoid–Induced Contractions of Rat Gatric Fundus Muscle by SC–19220 Sodium Meclofenamate, Indomethacin or Trimethoquinol," *Br. J. Pharmac.*, 71, 169–175 (1980)–London.

W. E. Coyne, et al. "Anticonvulsant Semicarbazides," *J. Med. Chem.*, 11(6), 1158–1160 (1968)–USA.

E. J. Drower, et al. "The Antiociceptive Effects of Prostaglandin Antagonists in the Rat," *European Journal of Pharmacology*, 133, 249–256 (1987)–Europe.

F. R. George, et al. "Antagonism of Alcohol Hypnosis by Blockade of Prostaglandin Synthesis and Activity: Genotype and Time Course Effects," *Pharmacology, Biochemistry & Behavoir*, vol. 19, 131–136 (1993)–USA.

R. Gimet, et al. "Quantitative Determination of Polymorphic Forms in a Formulation Matrix Using the Near Infra–Red Reflectance Analysis Technique," *Journal of Pharmaceutical & Biomedical Analysis*, vol. 5, No. 3, 205–211 (1987)–Great Britain.

A. Gomes, et al. "Pharmacodynamics of Venon of the Centipede *Scolopendra Subspinipes Dehaani*,"*Indian Journal of Experimental Biology*, vol. 20, 615–618, Aug. (1982)–India.

K. Gyrires, et al. "The Use of the Writhing Test in Mice for Screening Different Types of Analgesics," Arch. Int. Pharmacodyn, 267, 131–140 (1984)–USA.

D. E. MacIntyre, et al. "Antagonism of Human Platelet Responses to Stimulatory and Inhibitory Prostaglandins," *Prog. Lipid. Res.*, 20 (1–4), 453–9 (1981)–USA.

C. A. Maggi, et al. "The Effect of SC–19220, a Prostaglandin Antagonist, on the Micturition Reflex in Rats," *European Journal of Pharmacology*, 152, 273–279 (1988)–Europe.

K. Nagarajan, et al. "Synthesis of 10,11–Dihydrodibenz[b,f][1,4]oxazepine Derivatives as Potential Anticonvulsant & Psychotropic Agents," *Indian Journal of Chemistry*, vol. 24B, 840–844 (1985)–India.

S. Nakajyo, et al. "Inhibitory Effect of Bassianolide, a Cyclodepsipeptide, on Drug–Induced Contractions of Isolated Smooth Muscle Preparations," *Japan J. Pharmacol.*, 32, 55–64 (1982)–Japan.

A. Rakovska, et al. "Antagonistic Effect of SC–19220 on the Responses of Guinea–Pig Gastric Muscles to Prostaglandins, $E_1$, $E_2$, and $F_{2\alpha}$," *Arch. Int. Pharmacodyn.*, 268, 59–69 (1984)–USA.

J. H. Sanner "Dibenzoxazepine Hydrazides as Prostaglandin Antagonists," *Intra–Science Chem. Rept.*, vol. 6, No. 1, 1–9 (1972)–USA.

J. H. Sanner, et al. "Structure–Activity Relationships of Some Dibenzoxazepine Derivatives as Prostaglandin Antagonists," *Advances in the Biosciences*, 9, 139–148 (1972)–USA.

L. H. Werner, et al. "Imidazoline Derivatives with Antiarryhthmic Activity," *Journal of Med. Chem.*, vol. 10(4), 575–582, Jul., (1967)–USA.

L. H. Werner, et al. "38–Heterocyclic Compounds: Thiazepine Derivatives," *Chemical Abstracts*, 8325–8236 (1964)–USA.

2,3-,4-,5-,6-,7-,8-,9- AND/OR 10-SUBSTITUTED DIBENZOXAZEPINE COMPOUNDS, PHARMACEUTICAL COMPOSITIONS AND METHODS OF USE

BACKGROUND OF THE INVENTION (1) Field of the Invention

The present invention generally relates to compounds having pharmacological activity which are useful as pharmaceutical agents and, more particularly, as analgesic agents for the treatment of pain, and as Prostaglandin-$E_2$ antagonists for the treatment of prostaglandin-$E_2$ mediated diseases, to pharmaceutical compositions containing one or more of these compounds, and to methods of treatment employing these compounds. More particularly, the present invention concerns substituted dibenzoxazepine compounds, pharmaceutical compositions containing one or more of these compounds in combination with a pharmaceutically-acceptable carrier, and medical methods of treating pain and prostaglandin-$E_2$ mediated diseases employing these compounds.

Analgesic compounds are agents which alleviate pain without causing a loss of consciousness and, thus, which are useful for treating pain and, often, for reducing inflammation.

The major classes of analgesic compounds include narcotic analgesics, or opiates, compounds which alleviate pain and induce sleep, and analgesic-antipyretic compounds, compounds which alleviate pain and reduce fever, such as salicylates.

Although the efficacy of opiates in relieving pain is well established, the associated addiction liability of opiates is a distinct disadvantage of these compounds.

While salicylate and salicylate-like agents (non-steroidal antiinflammatory agents or NSAIDS) are also efficacious in relieving pain, they often exhibit undesirable side effects, such as gastrointestinal irritation, as with aspirin, allergic response, as with aspirin, and/or liver toxicity with extended use, as with acetaminophen.

The compounds of the present invention are neither opiates nor salicylates, and represent another class of compounds which are useful as analgesic agents.

(2) Description of the Related Art

U.S. Pat. No. 2,852,528 discloses 11-unsubstituted 10-(tertiary aminoalkyl)-dibenzo-[b:f]-thia-[1]-aza-[4]-cycloheptadiene-[2,6]-compounds.

U.S. Pat. No. 4,290,953 discloses dibenz[b,f][1,4]oxazepine derivatives which are stated to have serum cholesterol lowering activity, serum lipid lowering activity, blood lipid peroxide lowering activity and antiaggregation of platelet activity.

U.S. Pat. No. 3,534,019 discloses compounds which are hydrazides of tricyclic N-carboxylic acids.

U.S. Pat. No. 4,379,150 discloses dibenz[b,f][1,4]oxazepine derivatives which may have a heterocyclic ring present in the side chain at the 10-position of the molecule.

European Patent Application Publication No. 0 480 641 A1 discloses tricyclic heterocycles which are stated to have anti-hyperalgesic properties.

Each of the documents described hereinabove discloses compounds which are structurally different from the compounds of the present invention. Thus, the compounds of the present invention are structurally distinct from that which has been described in the art.

SUMMARY OF THE INVENTION

The present invention provides compounds having a structure of Formula I:

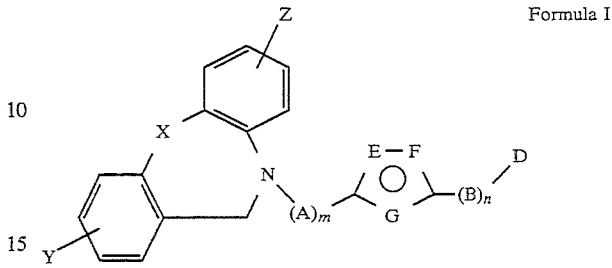

Formula I

Formula I or a pharmaceutically-acceptable salt thereof, wherein
X is oxygen, sulfur,

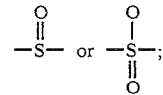

Y and Z may be the same or different, and may be hydrogen, hydroxy, alkoxy, halogen, —CN, —$NO_2$, —$NH_2$, alkylamino, arylamino or —$CF_3$;

A is —$CH_2$— or

E and F may be —CH=, oxygen, nitrogen or sulfur, and may not be the same;

G is oxygen, nitrogen or sulfur;

B is alkylene, alkylene-S-alkylene, alkylene-O-alkylene,

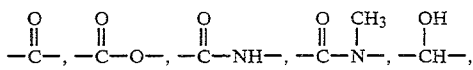

D is hydrogen, halogen, alkyl, hydroxy, dihydroxy, alkoxy, amino, alkylamino,

aryl, alkylaryl,

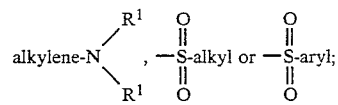

R is hydroxy, alkoxy or —NH-alkylaryl;
$R^1$ is hydrogen or alkyl;
m is an integer of from 0 to 4; and
n is an integer of from 0 to 4,
with the proviso that when G is oxygen or sulfur, one of E or F is nitrogen.

The present invention also provides pharmaceutical compositions which are pharmaceutically acceptable and which comprise a therapeutically-effective amount of a compound of Formula I in combination with a pharmaceutically-acceptable carrier, and a method for eliminating or ameliorating pain in an animal, or for treating a prostaglandin-$E_2$ mediated disease, comprising administering a therapeutically-effective amount of a compound of Formula I to the animal.

DETAILED DESCRIPTION OF THE INVENTION (1) Definitions

For purposes of clarity, the terms and phrases used throughout this specification and the appended claims are defined in the manner set forth directly below.

Some of the chemical structures which are presented in this specification and the appended claims have been drawn using the convention which employs lines to represent alkyl radicals, which is known by those of skill in the art.

All of the compounds of the invention shown and discussed in the examples may be identified by a bolded number and/or letter. The bolded number and/or letter refers to that compound shown and discussed in that example which has an example number and/or letter which corresponds to the bolded number and/or letter.

The abbreviations "AcOH" and "HOAc" as used herein mean acetic acid.

The abbreviation "Ac" and the term "acetyl" as used herein mean

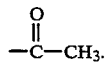

The abbreviation "AIBN" as used herein means 2,2'-azobis(2-methylpropionitrile).

The term "alkyl" as used herein means a saturated hydrocarbon radical having from one to ten carbon atoms, and within which includes from one to six carbon atoms, and further within which includes from one to three carbon atoms, which can be a straight or branched chain. Representative of such radicals are methyl, ethyl, propyl, isopropyl, butyl, sec-butyl, isobutyl, tert-butyl, pentyl and the like.

The term "alkylamino" as used herein means an alkyl group, as defined above, which has an amino group, as defined below, attached thereto.

The term "alkylaryl" as used herein means an alkyl group, as defined above, which has an aryl group, as defined below, attached thereto.

The term "alkylene" as used herein means a straight or branched saturated hydrocarbon chain spacer arm which has from one to ten carbon atoms, and within which includes from one to six carbon atoms, and further within which includes from one to three carbon atoms.

The term "alkoxy" as used herein means an alkyl radical, as defined above, having an oxygen atom attached thereto. Representative alkoxy groups include methoxy, ethoxy, propoxy, tert-butoxy and the like.

The term "alkoxycarbonyl" as used herein means an alkoxy group, as defined above, having a carbonyl group, as defined below, attached thereto.

The abbreviation "AlMe₃" as used herein means trimethylaluminum.

The term "amino" as used herein means an —NH₂ group.

The term "aminocarbonyl" as used herein means a carbonyl group, as defined below, which has an amino group, as defined above, attached thereto.

The term "amido" as used herein means a

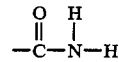

group.

The term "analgesia" as used herein means the reduction, or absence, of sensibility to pain, designating particularly the relief of pain without loss of consciousness.

The term "animal" as used herein includes mammals and nonmammals, and further includes humans and non-human mammals.

The term "aryl" as used herein means 5- and 6-membered single-ring aromatic radicals which may include from zero to four heteroatoms, and within which includes from zero to two heteroatoms, and further within which includes from zero to one heteroatom. Representative aryls include phenyl, thienyl, furanyl, pyridinyl, imidazolyl, thiazolyl, pyrimidinyl, pyrazinyl, pyridazinyl, (is)oxazolyl, triazolyl, tetrazolyl, pyrrolyl, pyridinyl-N-oxide and the like.

The term "arylamino" as used herein means an aryl group, as defined above, which has an amino group, as defined above, attached thereto.

The abbreviation "Boc" as used herein means t-butyloxycarbonyl.

The abbreviation "Calc." as used herein means calculated.

The term "carbonyl" as used herein means a

group.

The term "carboxy" as used herein means a

group.

The term "composition" as used herein means a product which results from the combining of more than one element or ingredient.

The term "cyano" as used herein means a —CN group.

The abbreviation "DCC" as used herein means dicyclohexylcarbodiimide.

The abbreviation DCM as used herein means dichloromethane.

The abbreviation DEAD as used herein means diethyl azodicarboxylate.

The abbreviation "DMAc" as used herein means dimethylacetamide.

The term "dialkylamino" as used herein means an amino group, as defined above, which has both of the hydrogen atoms replaced by an alkyl group, as defined above.

The abbreviation "DMA" as used herein means dimethylacetamide.

The abbreviation "DMAP" as used herein means 4-(dimethylamino)pyridine.

The abbreviation "DMF" as used herein means dimethylformamide.

The abbreviation "DSC" as used herein means Differential Scanning Calorimetry.

The phrase "$EC_{50}$ concentration" as used herein means that concentration of a compound or drug which is necessary to elicit a 50% maximal biological response and, thus, which is necessary to elicit a 50% reduction in the contractions of guinea pig ileum segments in a prostaglandin antagonism assay.

The phrase "$ED_{50}$ dose" as used herein means that dose of a compound or drug which produced a biological effect, such as producing analgesia, in 50% of the animals to which the compound or drug was administered.

The abbreviation "EDC" as used herein means N,N-dimethylaminopropylethylcarbodiimide hydrochloride.

The abbreviation "Et" as used herein means ethyl ($-CH_2CH_3$).

The abbreviation "EtOAc" as used herein means ethyl acetate.

The abbreviation "EtOH" as used herein means ethanol ($CH_3CH_2OH$).

The abbreviation "$Et_3N$" as used herein means triethylamine.

The abbreviation "$Et_2O$ as used herein means diethylether.

The abbreviation "Gly" as used herein means glycine. The term "halo" or "halogen" as used herein means chlorine (Cl), bromine (Br), fluorine (F) and/or iodine (z).

The term "heteroatom" as used herein means an atom of any element other than carbon or hydrogen.

The abbreviation "$^1H$ NMR" as used herein means Proton Nuclear Magnetic Resonance.

The abbreviation "HPLC" as used herein means High Pressure Liquid Chromatography.

The abbreviation "HOBT" as used herein means hydroxybenzotriazole.

The term "hydroxy" as used herein means the group $-OH$.

The term "intragastrically" and/or the abbreviation "i.g." as used herein means that a compound or drug was administered into the stomach.

The abbreviation "i.p." as used herein means that a compound or drug was administered intraperitoneally.

The abbreviation "i-$Pr_2EtN$" as used herein means N,N-diisopropylethylamine.

The abbreviation "IR" as used herein means infrared, referring to an infrared spectrum.

The abbreviation "LAH" as used herein means lithium aluminum hydride.

The abbreviation "Me" as used herein means methyl ($-CH_3$).

The abbreviation "MeOH" as used herein means methanol ($CH_3OH$).

The abbreviation "mp" as used herein means melting point.

The abbreviation "MPLC" as used herein means Medium Pressure Liquid Chromatography.

The abbreviation "NBS" as used herein means N-bromosuccinimide.

The term "nitro" as used herein means an $-NO_2$ group.

The abbreviation "n-BuLi" as used herein means n-butyl lithium.

The abbreviation "NMR" as used herein means Nuclear Magnetic Resonance.

The abbreviation "n-Pr" as used herein means n-propyl.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, as defined directly above, such as a liquid or solid filler, diluent, excipient, solvent or encapsulating material, involved in carrying or transporting a chemical compound or pharmaceutical agent from one organ, or portion of the body, to another organ, or portion of the body. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The phrase "pharmaceutically-acceptable salts" as used herein refers to non-toxic salts of the compounds of the present invention which are generally prepared by reacting the free base with a suitable organic or inorganic acid, or which are prepared by reacting the free acid with a suitable base. Representative salts include the hydrochloride, hydrobromide, sulfate, bisulfate, acetate, valerate, oleate, palmitate, stearate, laurate, benzoate, lactate, phosphate, tosylate, citrate, maleate, fumarate, succinate, tartrate, napsylate, clavulanate and the like salts, and alkali metal salts, such as sodium and potassium, and alkaline earth salts, such as calcium and magnesium.

The abbreviation "Ph" as used herein means phenyl (the group $C_6H_5-$ derived from benzene).

The abbreviation "p.o." as used herein means that a compound or drug was administered orally.

The phrase "protecting group" as used herein means substituents which protect the reactive functional group from undesirable chemical reactions. Examples of such protecting groups include esters of carboxylic acids, ethers of alcohols and acetals and ketals of aldehydes and ketones.

The phrase "N-protecting group" or "N-protected" as used herein means those groups intended to protect the N-terminus of an amino acid or peptide, to protect an amino group against undesirable reactions during synthetic procedures and includes, but is not limited to, sulfonyl, acetyl, pivaloyl, t-butyloxycarbonyl (Boc), carbonylbenzyloxy (Cbz), benzoyl and an L- or D-aminoacyl residue, which may itself be N-protected similarly.

The abbreviation "RaNi" as used herein means Raney nickel.

The abbreviation "Rh" as used herein means rhodium.

The abbreviation "s.c." as used herein means that a compound or drug was administered subcutaneously.

The term "sulfonyl" as used herein means an

group.

The abbreviation "t-Bu" as used herein means tert-butyl.

The abbreviation "TEA" as used herein means triethylamine.

The abbreviation "THF" as used herein means tetrahydrofuran.

The phrase "therapeutically-effective amount" as used herein means an amount of a compound, material, or composition which is an effective dose for eliminating or ameliorating pain in an animal, or for producing some other desired therapeutic effect, at a reasonable benefit/risk ratio applicable to any medical treatment.

The phrases "title compound," "title product" and "title material" as used herein mean that compound, product or material whose chemical name is given, and/or whose structure is shown, in the particular example, or subpart thereof, referred to. If no particular example, or subpart thereof, is referred to, it means that compound, product or material whose chemical name is given, and/or whose structure is shown, in the particular example, or subpart thereof, in which it appears.

The term "trifluoromethyl" as used herein means a —CF$_3$ group.

(2) Description of Invention

In one aspect, the present invention provides compounds comprising a structure of Formula I, as described above, and pharmaceutically-acceptable salts thereof.

The compounds of the present invention comprise a class of substituted dibenzoxazepine compounds in which the 2-, 3-, 4-, 5-, 6-, 7-, 8-, 9- and/or 10-position is substituted. Compounds within the present invention have been shown to exhibit activity as prostaglandin E$_2$ antagonists.

Specific compounds within the scope of the invention include, but are not limited to, the compounds discussed in the examples presented below, as well as their pharmaceutically-acceptable salts.

Contemplated equivalents of the compounds described in Formula I include compounds which otherwise correspond thereto, and which have the same general properties thereof, wherein one or more simple variations of substituents are made which do not adversely affect the efficacy of the compound.

Certain compounds of this invention may exist in geometric or stereoisomeric forms. The present invention contemplates all such compounds, including cis- and trans- geometric isomers, R- and S-enantiomers, diastereomers, d-isomers, l-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Certain compounds of the present invention may contain a basic functional group, such as amino, alkylamino or dialkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, S. M. Berge et al., "Pharmaceutical Salts," "J. Pharm. Sci., 66, 1–19 (1977), which, as well as all other documents referred to herein, is incorporated herein by reference.)

In other cases, the compounds of the invention may contain one or more acidic functional groups, such as carboxyl and the like, and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, S M Berge et al , "Pharmaceutical Salts," supra.)

In another aspect, the present invention provides pharmaceutically-acceptable compositions which comprise a therapeutically-effective amount of one or more of the compounds of Formula I, as described hereinabove, formulated together with one or more pharmaceutically-acceptable carriers. The pharmaceutical compositions of the invention may be specially formulated for oral administration in solid or liquid form, for parenteral injection, or for rectal or vaginal administration.

In yet a further aspect, the present invention provides a method for eliminating or ameliorating pain in an animal, or for producing some other therapeutic effect, as discussed in more detail hereinbelow, comprising administering a therapeutically-effective amount of a compound of Formula I, as described hereinabove, to the animal.

The preferred embodiments of this invention are the compounds described in Examples 7, 9, 11, 15, 20, 21, 26, 27, 28, 29, 32, 34A, 34B and 36. The most preferred embodiment of the invention is the compound described in Example 15 below.

(3) Utility

Compounds of the present invention have been found to exhibit activity as prostaglandin $E_2$ antagonists (prostaglandin antagonists of the $E_2$ series).

Compounds within the present invention, and the pharmaceutical compositions comprising one or more of these compounds, are useful as analgesic agents for the elimination or amelioration of pain in animals.

In addition to treating pain, these compounds and compositions would be useful in treating prostaglandin-$E_2$ mediated diseases, such as convulsions, ischemia and other central nervous system disorders, as well as osteoporosis, dysmenorrhea, asthma, enuresis, arrhythmia, urinary incontinence, gastric hypermotility, irritable bowel syndrome and diarrhea, by virtue of their activity as prostaglandin $E_2$ antagonists.

(4) Methods of Preparation

In general, the compounds of the present invention may be prepared by the methods illustrated in the following general reaction schemes, or by modifications thereof, using readily available starting materials, reagents and conventional synthesis procedures. Unless otherwise specified, the various substituents of the compounds are defined in the same manner as they are defined above in Formula I in the "Summary of Invention" section.

If a particular enantiomer of a compound of the present invention is desired, it may be prepared by chiral synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

In General Reaction Scheme No. 1, substituted salicaldehyde or thiosalicaldehyde (wherein X is oxygen or sulfur and wherein Y, which can be the same as Z or different from Z, is hydrogen, hydroxy, alkoxy, halogen, —CN, —NO$_2$, —NH$_2$, alkylamino, arylamino or —CF$_3$) is reacted with base, and to this is added a substituted 2-chloronitrobenzene (wherein Z is hydrogen, halogen, hydroxy, alkoxy, —CN, —NO$_2$, —NH$_2$, alkylamino, arylamino or —CF$_3$). The resulting ether (or thioether) is reduced to yield substituted dibenzoxazepine (dibenzothiazepine), wherein Y and Z are as described hereinabove. If dibenzothiazepine, oxidation of the sulfur is achieved with hydrogen peroxide.

In General Reaction Scheme No. 2, a substituted or unsubstituted dibenz[b,f][1,4]oxazepine was treated with methyllithium followed by methoxymethylisothiocyanate to provide a thiourea which was heated with a molar equivalent of ethyl bromopyruvate in an alcohol solvent to give a 4-thiazolecarboxylic acid ethyl ester (Compound-I). The ester group in Compound-I was hydrolyzed using lithium hydroxide to provide an acid (Compound-II). The mixed anhydride prepared by treating Compound-II with isobutyl chloroformate in the presence of 4-methylmorpholine on reaction with amines gave the amides. Hydrochloride salts of the amides can be prepared by dissolving the amides in solvents containing hydrogen chloride or hydrochloric acid. In General Reaction Scheme No. 2, X is oxygen, sulfur,

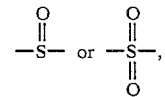

and Y and Z may be as described above for General Reaction Scheme No. 1. Where X is sulfur, oxidation of the sulfur may be achieved with hydrogen peroxide.

In General Reaction Scheme No. 3, the N-methoxy-N-methylamine amide (Compound-III) of the 4-thiazole carboxylic acid (Compound-II of General Reaction Scheme No. 2) was prepared as described in General Reaction Scheme No. 2. This amide was reacted with the lithiated acetylenic pyridine (prepared by reacting one equivalent of butyllithium with an ethynylpyridine) to give a propargylic ketone. Hydrogenation of the triple bond gave the desired ketonic derivatives. Hydrochloride salts of the ketones can be prepared by dissolving the ketones in solvents containing hydrogen chloride or hydrochloric acid. In General Reaction Scheme No. 3, X, Y and Z are as described above in General Reaction Scheme No. 2.

In General Reaction Scheme No. 4, the ester functionality in the 4-thiazolecarboxylic acid ethyl ester (Compound-I in General Reaction Scheme No. 2) was reduced with diisobutylaluminium hydride to give a mixture of the corresponding aldehyde (Compound-IV) and alcohol (Compound-V). Reaction of Compound-IV with lithiated acetylene (prepared as described for General Reaction Scheme No. 3) gave a propargyl alcohol. Hydrogenation of the triple bond in the propargyl alcohol gave a mixture of cis allyl alcohol and a saturated alcohol which were separated by chromatography over silica gel. Hydrochloride salts of these alcohols can be prepared by dissolving the alcohols in solvents containing hydrogen chloride or hydrochloric acid. In General Reaction Scheme No. 4, X, Y and Z are as described above for General Reaction Scheme No. 1.

In General Reaction Scheme No. 5, Compound-V from General Reaction Scheme No. 4 on reaction with triphenylphosphine, diethylazodicarboxylate and diphenoxyphosphorylazide gave an azide derivative which was reduced with lithium aluminium hydride to the corresponding amine (Compound-VI). Reaction of Compound-VI with activated carboxylic acids like acid chloride gave the corresponding amides. Hydrochloride salts of these amides can be prepared by dissolving the amides in solvents containing hydrogen chloride or hydrochloric acid.

In General Reaction Scheme No. 6, to a solution of 4- or 5-carboxyethyl-2-methyloxazole is added N-bromosuccinimide and AIBN. After heating and shining a sun lamp on the reaction for four hours, the product is isolated.

In General Reaction Scheme No. 7, tribromoimidazole is treated with an alkyl halide to protect the ring nitrogen. The protected imidazole is treated at −78° C. with n-BuLi and DMF. The subsequent aldehyde is reduced and the resulting alcohol is protected. The dibromoimidazole is treated at −78° C. with n-BuLi and 2-propanol and then is treated again at −78° C. with n-BuLi and ethyl chloroformate. The protecting group on the alcohol is removed, followed by the bromination of the alcohol. The resulting bromide is used in General Reaction Scheme No. 8.

In General Reaction Scheme No. 8, to the appropriately-substituted dibenzoxazepine or dibenzothiazapine dissolved in toluene is added 4- or 5-carboethoxy-2-bromomethyl-oxazole or -thiazole or -imidazole. The above solution in the presence of a tertiary amine is heated at 110° C. for 20 hours. The product ester in toluene or dichloromethane is treated with an amine in the presence of trimethylaluminum. After heating for sixteen hours, the product is isolated from the reaction mixture to yield final product. In the case of imidazole, the protecting group is removed with 3N HCl to yield final product. In General Reaction Scheme No. 8, X, Y and Z are as described above for General Reaction Scheme No. 1.

In General Reaction Scheme No. 9, the ester described in General Reaction Scheme No. 7 is hydrolyzed by treatment with 1N NaOH. The resulting acid is activated and coupled to an amine to yield final product. In General Reaction Scheme No. 9, X, Y and Z are as described above for General Reaction Scheme No. 1, and E is —CH, oxygen, nitrogen or sulfur.

In General Reaction Scheme No. 10, the acid shown therein is treated with triphenylphosphine and diethyl azodicarboxylate in the presence of an appropriate alcohol. The ester is isolated and treated to remove the protecting group. In General Reaction Scheme No. 10, X, Y, Z and E are as described above for General Reaction Scheme No. 9.

In General Reaction Scheme No. 11, to the appropriately-substituted dibenzoxazepine or dibenzothiazapine dissolved in toluene is added 4- or 5-carboethoxy-2-substituted-oxazole or -thiazole or -imidazole. The above solution in the presence of a trimethylaluminum is heated at 110° C. for 20 hours. At the end of this time, the product is isolated. In General Reaction Scheme No. 11, X, Y and Z are as described above for General Reaction Scheme No. 1.

In General Reaction Scheme No. 12, to an N-substituted-dibenzothiazepine in acetic acid is added hydrogen peroxide. The sulfoxide is isolated after one hour. To obtain the sulfone, the hydrogen peroxide solution is heated at 50° C. In General Reaction Scheme No. 12, Y and Z are as described above for General Reaction Scheme No. 1.

GENERAL REACTION SCHEME NO. 1

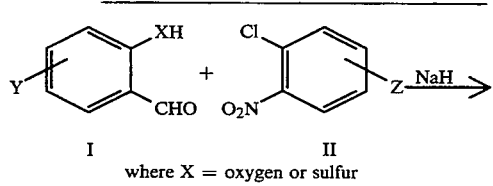

I   II
where X = oxygen or sulfur

-continued
GENERAL REACTION SCHEME NO. 1

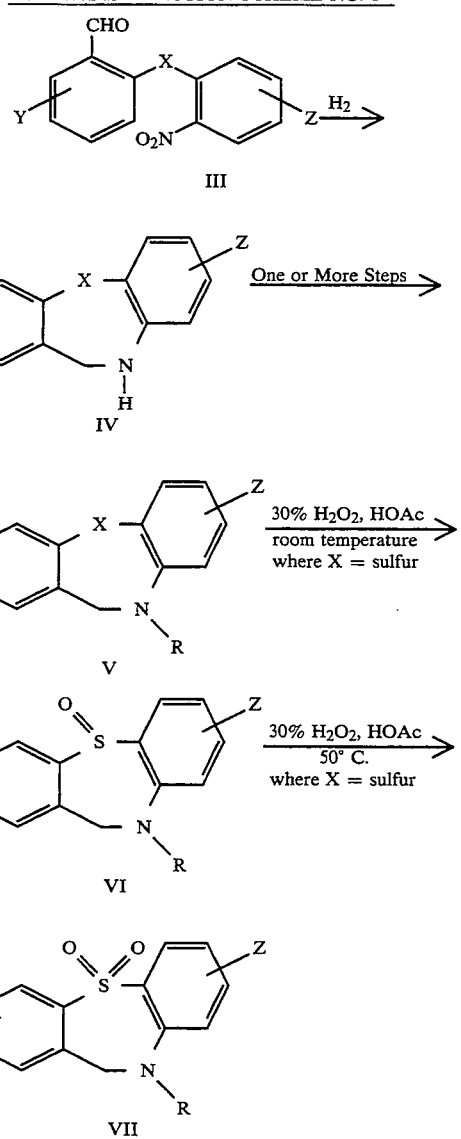

R = appropriately substituted five membered aromatic heterocycle

GENERAL REACTION SCHEME NO. 2

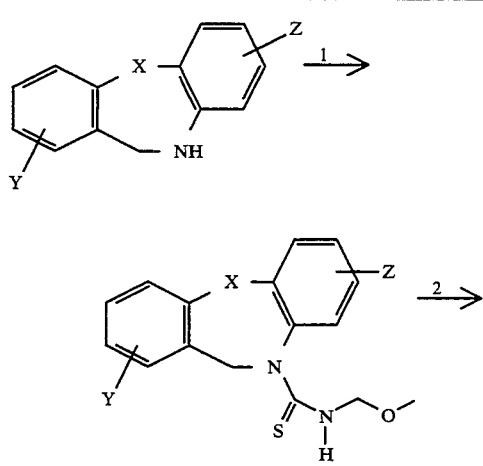

-continued
GENERAL REACTION SCHEME NO. 2

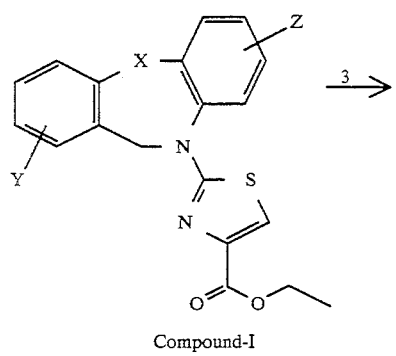

Compound-I

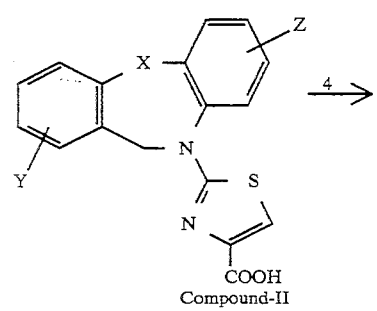

Compound-II

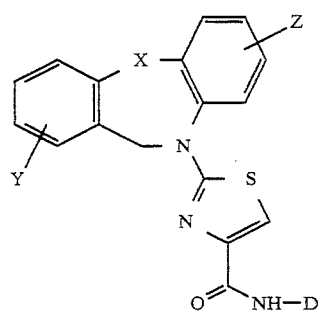

Key:
1. Methyl lithium, methoxymethylisothiocyanate, THF.
2. Ethyl bromoacetate, ethanol.
3. Lithium hydroxide, ethanol, water.
4. Isobutylchloroformate, 4-methylmorpholine, THF or CH$_2$Cl$_2$ and then amine (—NH—D).

GENERAL REACTION SCHEME NO. 3

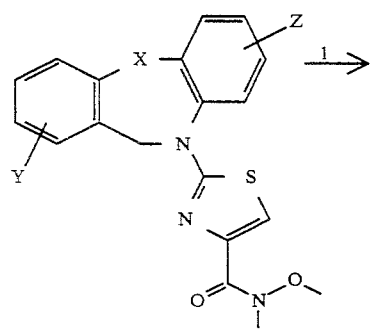

Compound-III

-continued
GENERAL REACTION SCHEME NO. 3

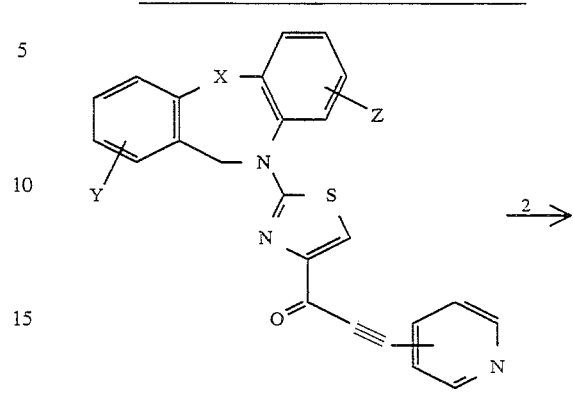

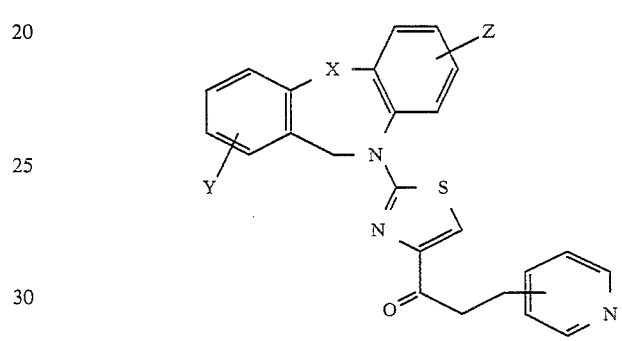

Key
1. Add the thiazole amide to lithiated ethynylpyridine prepared from ethynylpyridine and n-butyl lithium.
2. Raney-Nickel, 5 atmosphere pressure H$_2$, ethyl acetate.

GENERAL REACTION SCHEME NO. 4

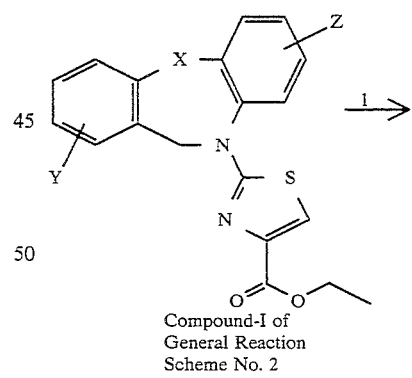

Compound-I of
General Reaction
Scheme No. 2

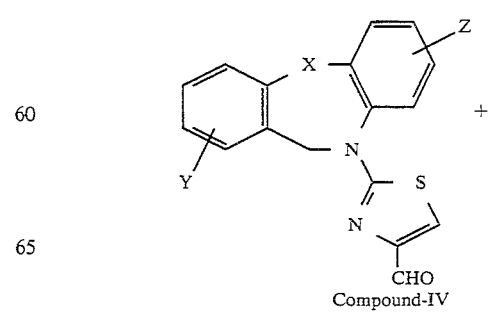

Compound-IV

-continued
GENERAL REACTION SCHEME NO. 4
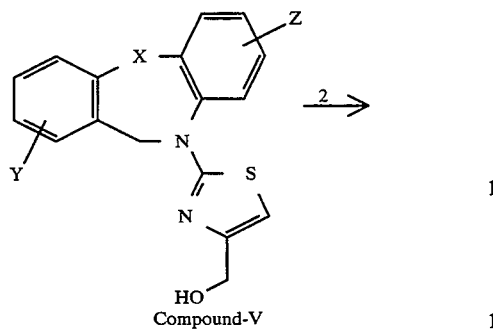
Compound-V
2 →
-continued
GENERAL REACTION SCHEME NO. 4
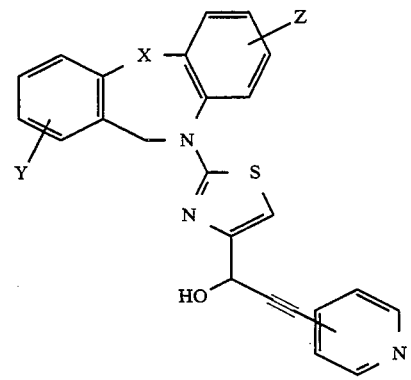
GENERAL REACTION SCHEME NO. 4
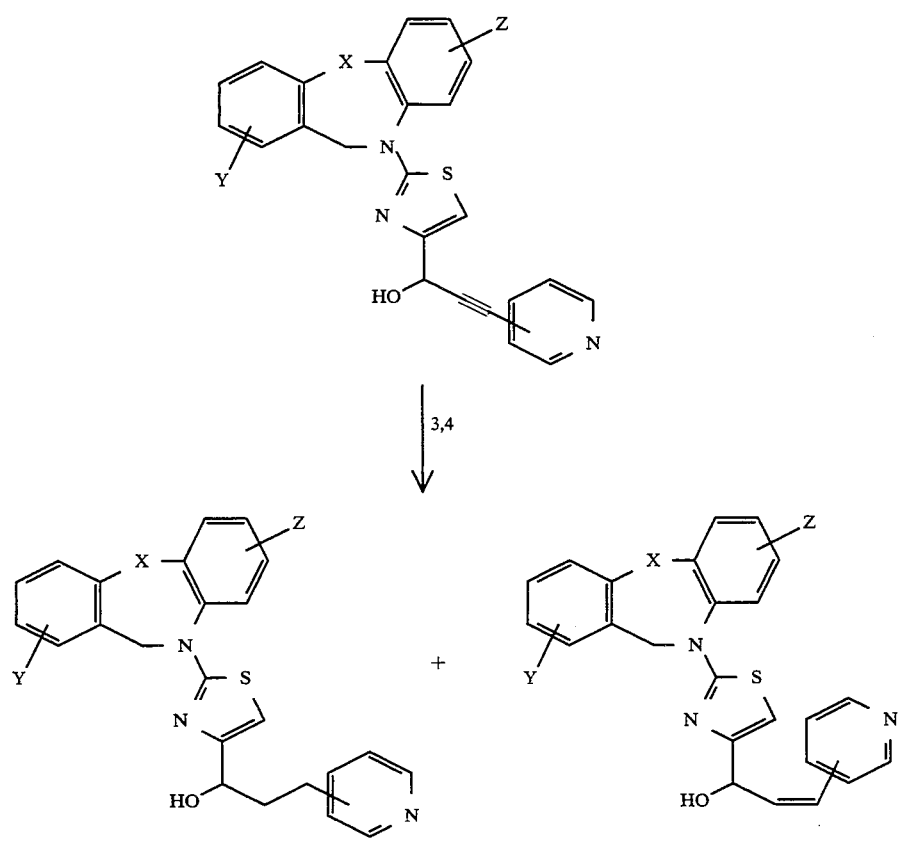
Key
1. Diisobutyl aluminium hydride.
2. Lithiated ethynylpyridine prepared from ethynylpyridine and n-butyl lithium.
3. Raney-Nickel, 5 atmosphere pressure H₂.
4. Seperate by chromatography.

GENERAL REACTION SCHEME NO. 5

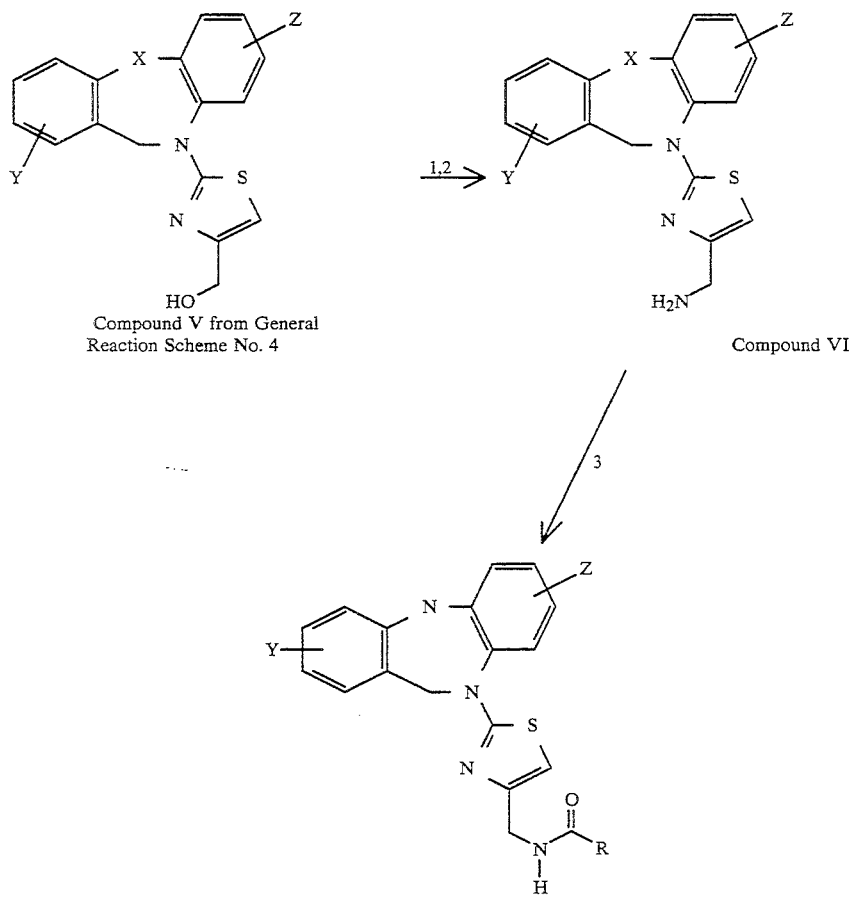

Compound V from General Reaction Scheme No. 4

Compound VI

Key:
1. Triphenylphosphine, diphenoxyphosphoryl azide, diethylazidodicarboxylate, THF.
2. Lithium aluminium hydride, THF.
3. Add the thiazole amine to mixed anhydride prepared from carboxylic acid (R—COOH), Isobutyl chloroformate and 4-methylmorpholine in THF or $CH_2Cl_2$.

GENERAL REACTION SCHEME NO. 6

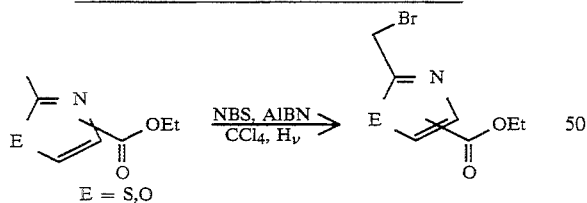

E = S, O

GENERAL REACTION SCHEME NO. 7

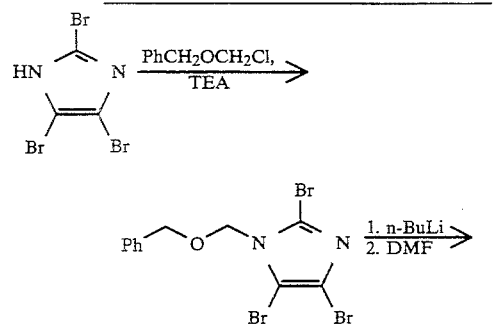

-continued
GENERAL REACTION SCHEME NO. 7

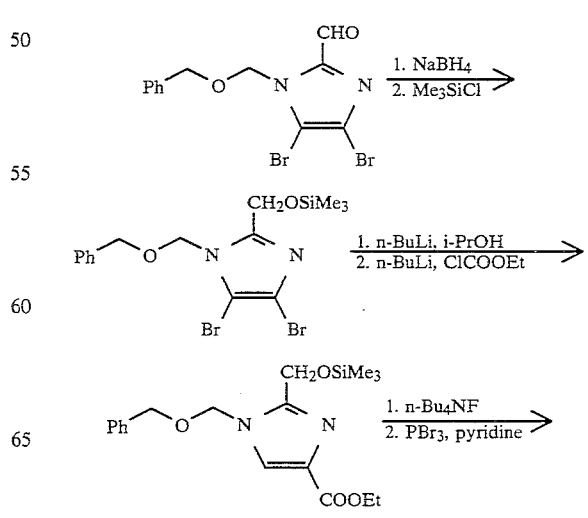

GENERAL REACTION SCHEME NO. 7
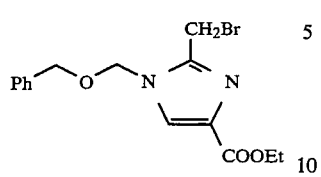
GENERAL REACTION SCHEME NO. 8
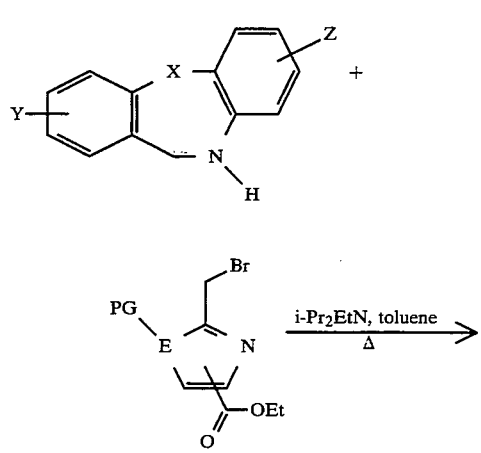
E = N, S, O
PG = protecting group in the case where E = N.
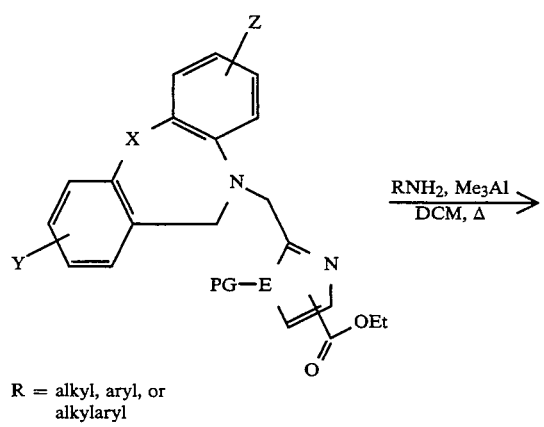
R = alkyl, aryl, or alkylaryl
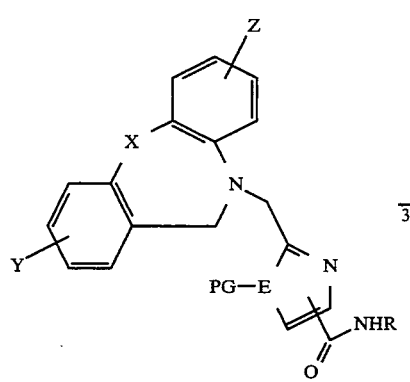
GENERAL REACTION SCHEME NO. 8
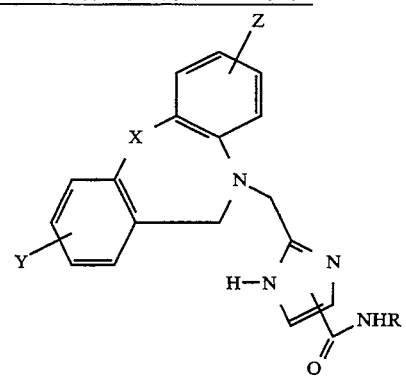
GENERAL REACTION SCHEME NO. 9
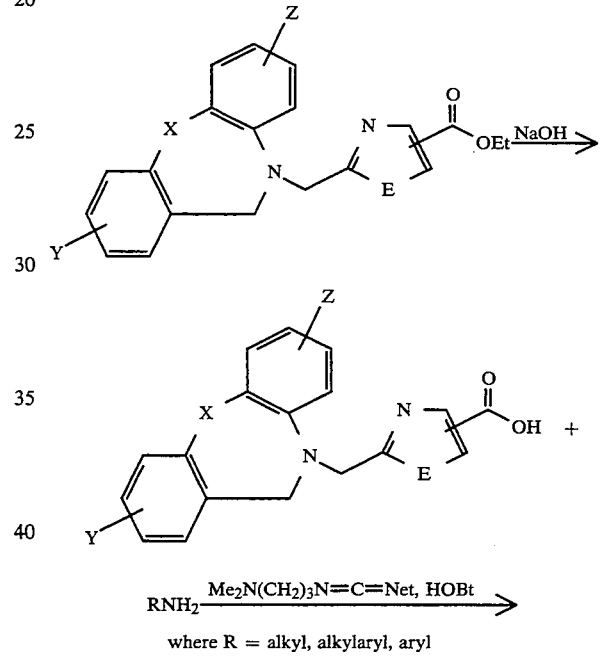
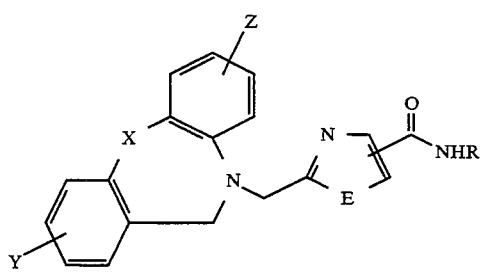
where R = alkyl, alkylaryl, aryl
GENERAL REACTION SCHEME NO. 10
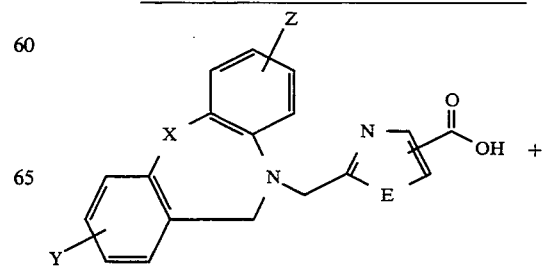

GENERAL REACTION SCHEME NO. 10

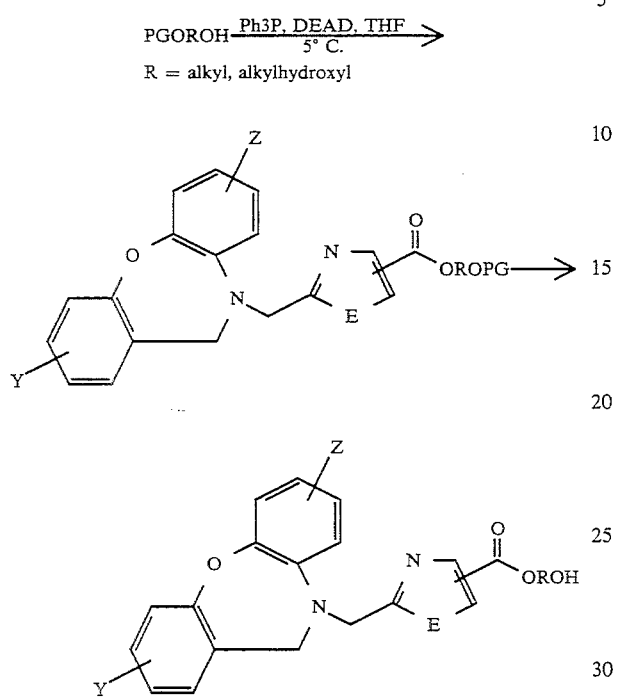

GENERAL REACTION SCHEME NO. 11

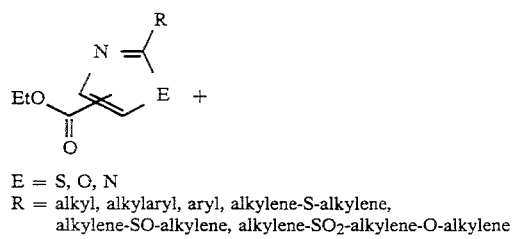

E = S, O, N
R = alkyl, alkylaryl, aryl, alkylene-S-alkylene, alkylene-SO-alkylene, alkylene-SO₂-alkylene-O-alkylene

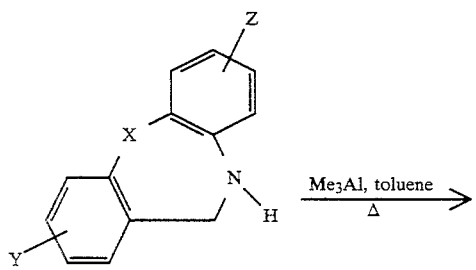

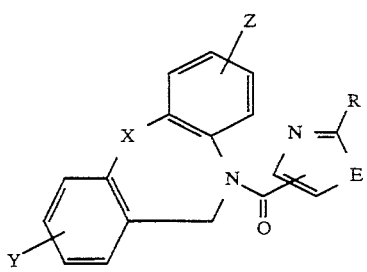

GENERAL REACTION SCHEME NO. 12

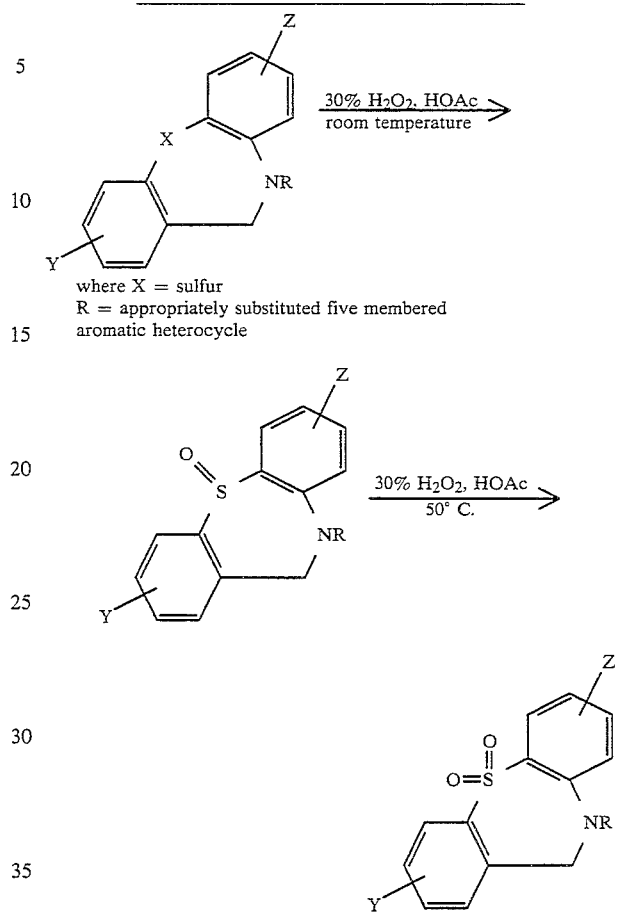

where X = sulfur
R = appropriately substituted five membered aromatic heterocycle The conditions for carrying out the individual steps in each of the general reaction schemes presented above are conventional, well-known, and capable of wide variation.

Other methods known in the art can also be used to synthesize the compounds of the present invention.

(5) Dosage and Mode of Administration

The compounds of the present invention, and the pharmaceutical compositions comprising one or more of these compounds in combination with a pharmaceutically-acceptable carrier, are useful in treating pain in animals. A physician or veterinarian of ordinary skill in the art can readily determine whether or not a patient is in pain.

The pharmaceutical compositions of the present invention, which will typically comprise one or more of the compounds of Formula I as an active ingredient in admixture with one or more pharmaceutically-acceptable carriers and, optionally, with one or more other compounds, drugs or materials, are employed therapeutically and, thus, would generally be used under the guidance of a physician. The appropriate dosage and form of administration of these compositions will be suitably selected by methods which are consistent with conventional pharmaceutical practices.

The pharmaceutical compositions of the present invention may be specially formulated for oral administration in solid or liquid form, for parenteral injection, and/or for rectal or vaginal administration. They may be administered to humans and other animals for therapy by any suitable route of administration, including orally, nasally, as by, for example, a spray, rectally, intravaginally, parenterally, intracisternally and topically, as by powders, ointments or drops, including buccally and sublingually. While the preferred routes of administration are orally and parenterally, the most preferred mode of administration is orally.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the salt thereof, the route of administration, the time of administration, the rate of excretion of the particular compound being employed, the severity of the pain, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required to alleviate or ameliorate a particular patient's pain. For example, the physician or veterinarian could start doses of the compound of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, dosage levels in the range of from about 0.001 mg to about 10 g, more preferably from about 1 mg to about 1000 mg, of active compound per kilogram of body weight per day are administered to a mammalian patient. However, the total daily usage of the compounds of Formula I, or the pharmaceutical compositions comprising such compounds, will be determined by an attending physician or veterinarian within the scope of sound medical judgement.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

The pharmaceutical compositions of the present invention comprise a compound of the present invention together with one or more pharmaceutically-acceptable carriers thereof and, optionally, with other therapeutic agents. Each carrier must be "acceptable" in the sense of being compatible with the other ingredients of the formulation and not injurious to the patient.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfite, sodium metabisulfite, sodium sulfite and the like; (2) oil-soluble antioxidants, such as ascorbyl palmitate, butylated hydroxyanisole (BHA), butylated hydroxytoluene (BHT), propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient (compound of Formula I) which can be combined with a carrier material to produce a single dosage form will vary depending upon the host being treated, the particular mode of administration and all of the other factors described above. The amount of active ingredient which can be combined with a carrier material to produce a single dosage form will generally be that amount of the compound which is the lowest dose effective to produce a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, with one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient (compound of Formula I) is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient (compound of Formula I as described above), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Opthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The injectable materials can be sterilized, for example, by filtration through a bacterial-retaining filter, or by incorporating sterilizing agents in the form of sterile solid compositions which can be dissolved or dispersed in sterile water or in other sterile injectable mediums just prior to use.

The formulations may be presented in unit-dose or multi-dose sealed containers, for example, ampoules and vials, and may be stored in a lyophilized condition requiring only the addition of the sterile liquid carrier, for example water for injections, immediately prior to use. Extemporaneous injection solutions and suspensions may be prepared from sterile powders, granules and tablets of the type described above.

The pharmaceutical compositions of the present invention may also be used in the form of veterinary formulations, including those adapted for the following: (1) oral administration, for example, drenches (aqueous or non-aqueous solutions or suspensions), tablets, boluses, powders, granules or pellets for admixture with feed stuffs, pastes for application to the tongue; (2) parenteral administration, for example, by subcutaneous, intramuscular or intravenous injection as, for example, a sterile solution or suspension or, when appropriate, by intramammary injection where a suspension or solution is introduced into the udder of the animal via its teat; (3) topical application, for example, as a cream, ointment or spray applied to the skin; or (4) intravaginally, for example, as a pessary, cream or foam.

While the various aspects of the present invention are described herein with some particularity, those of skill in the art will recognize numerous modifications and variations which remain within the spirit of the invention. These modifications and variations are within the scope of the invention as described and claimed herein.

(6) Examples

The following examples describe and illustrate the methods for the preparation of the compounds of the present invention, as well as other aspects of the present invention, and the results achieved thereby, in further detail. Both an explanation of, and the actual procedures for, the various aspects of the present invention are described where appropriate. These examples are intended to be merely illustrative of the present invention, and not limiting thereof in either scope or spirit. Those of skill in the art will readily understand that known variations of the conditions and processes of the preparative procedures described in these examples can be used to prepare the compounds of the present invention, and the pharmaceutical compositions comprising such compounds.

In the examples, all parts are by weight unless otherwise indicated.

All equipment employed in the examples is commercially available. Unless otherwise indicated, all starting materials employed in the examples are commercially available. Sources for these materials include Sigma Chemical Co. (St. Louis, Mo.), Aldrich Chemical Co. (Milwaukee, Wis.), Lancaster Synthesis (Windham, N.H.), Fisher Scientific (Pittsburgh, Pa.), Boehringer Mannheim Biochemicals (Indianapolis, Ind.), Fluka Chemical Corp. (Ronkonkoma, N.Y.), Chemical Dynamics Corp. (South Plainfield, N.J.) and Trans World Chemicals (Rockville, Md.). Most of the starting materials were obtained from Aldrich Chemical Co. (Milwaukee, Wis.).

All patents and publications referred to in the examples, and throughout the specification, are hereby incorporated herein by reference, without admission that such is prior art.

EXAMPLE 1

2-phenyl-4-chloromethyloxazole (1)

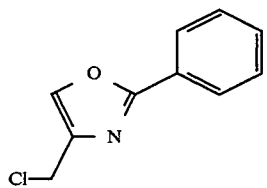

The synthesis of 1 is described in I. Smiti, E. Chindris, *Arch. Pharmaz.* 1971, 304, 425.

The solids, benzamide (12.1 g) and 1,3-dichloroacetone (12.6 g), were mixed together in a round bottomed flask and heated at 120° C. under an argon atmosphere for 2 hours. The reaction was cooled to 25° C. for 1 hour, followed by the addition of concentrated $H_2SO_4$ (50 mL). The resulting syrup was poured onto ice and the precipitate was filtered, washed with water and dried to yield 13.3 g of 1.

EXAMPLE 2

8-chloro-10,11-dihydro-10-[(2-phenyl-4-oxazolyl)methyl]dibenz[b,f][1,4]oxazepine (2)

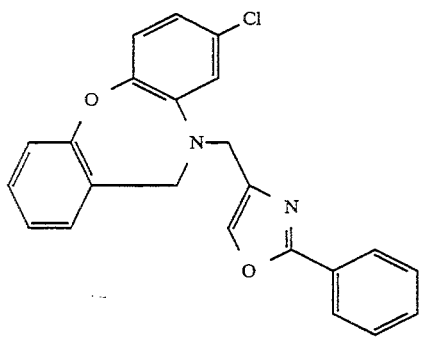

8-chloro-10,11-dihydrodibenz[b,f][1,4]oxazepine is synthesized in the manner described in U.S. Pat. No. 3,534,019, which is incorporated herein by reference.

Briefly, 200 parts of 2,5-dichloro-nitrobenzene were heated to 160° C. and stirred, and 160 parts of the potassium salt of salicylaldehyde was added over a period of 30 minutes. After the addition was complete, an exothermic reaction took place, and the temperature rose to about 195° C. Heating was discontinued until the reaction subsided, and the mixture was heated for 1 hour at 150° C. The mixture was cooled, ice and water were added, and it was extracted with ether. The ether layer was filtered to remove insoluble material, and the resultant solution was dried over sodium sulfate. The ether solvent was evaporated, and the residual oil was recrystallized from a mixture of hexane and benzene to give 2-(2-nitro-4-chloro-phenoxy)benzaldehyde melting at about 100°–101° C.

A solution of 55 parts of the ether obtained in the preceding paragraph in 800 parts of ethanol was hydrogenated over Raney nickel catalyst at room temperature and atmospheric pressure. When hydrogen uptake ceased, the catalyst was removed by filtration, and the ethanol solvent was evaporated. The residue was dissolved in 500 parts by volume of hexane, filtered, and cooled. There was obtained yellowish-white crystals which were separated by filtration to give 8-chloro-10,11-dihydrodibenz-[b,f][1,4]oxazepine melting at about 94°–95° C.

A mixture of 1 (1.85 g), 8-chlorodibenz[b,f][1,4]oxazepine (2.0 g), potassium carbonate (2.4 g) and potassium iodide (225 mg) in acetonitrile was refluxed for 24 hours. The solvent was removed under reduced pressure and the residue was partitioned between ethyl acetate (EtOAc) and H$_2$O, followed by extraction with HCl (1M) and brine (saturated), dried over anhydrous Na$_2$SO$_4$, and evaporated to yield an oil. The oil was purified by silica gel chromatography on medium pressure liquid chromatography (MPLC), which was eluted by a gradient of CH$_2$Cl$_2$:Hexane; 3:7 to CH$_2$Cl$_2$; 100% to yield an oil. The product was treated with ethanol (EtOH)/HCl and precipitated with diethylether (Et$_2$O) and placed under vacuum to yield a yellow foam (1.18 g). C, H, N, Cl calculated for C$_{23}$H$_{17}$N$_2$O$_2$Cl.0.05 HCl: Calculated: C: 70.71; H: 4.40; N: 7.17; Cl: 9.53. Found: C: 70.62; H: 4.57; N: 7.08; Cl: 9.59.

EXAMPLE 3

2-pentyl-4-chloromethyl-oxazole (3)

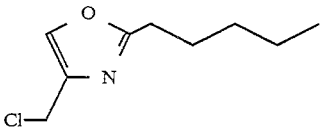

The synthesis of 3 was performed similarly to example 1 above. The solids, hexanoamide (5 g) and 1,3-dichloroacetone (5.5 g), were mixed together in a round bottomed flask and heated at 120° C. under an argon atmosphere for 2 hours. The mixture was cooled to 25° C. for 1 hour, followed by the addition of concentrated H$_2$SO$_4$ (50 mL). The resulting syrup was poured onto ice and the pH was adjusted to 10 with NaOH (1M). The resulting solution was extracted with CHCl$_3$, dried (Na$_2$SO$_4$) and evaporated to yield a brown liquid (1.56 g). This material was chromatographed according to Still et al. (*J. Org. Chem.*, 1978, 43, 2923) on silica gel in EtOAc to yield 3 as a yellow liquid (1.4 g).

EXAMPLE 4

10-[(2-pentyl-4-oxazolyl)methyl]-8-chloro-10,11-dihydrodibenz[b,f][1,4]oxazepine, monohydrochloride (4)

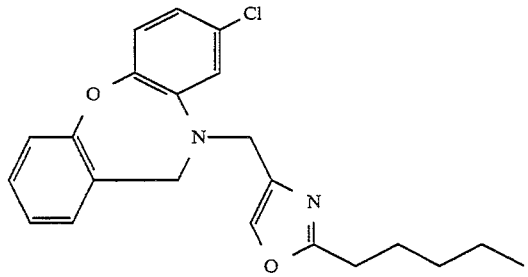

To a stirring solution of 8-chlorodibenz[b,f][1,4]oxazepine (617 mg) in 10 mL tetrahydrofuran (THF) under an argon atmosphere at −78° C. was added n-BuLi (1.1 mL, 2.5M). The solution was allowed to warm to 0° C. and then cooled to −78° C. followed by the addition of 3 (500 mg) in THF (4 mL). The reaction solution was allowed to warm to 25° C., poured onto EtOAc, extracted with brine, and dried (Na$_2$SO$_4$). The residue was flash chromatographed (silica gel, CH$_2$Cl$_2$:hexane (3:7)) to yield an oil (600 mg). The oil was dissolved in ether and precipitated by the dropwise addition of HCl/Dioxane. The resulting precipitate was collected and dried to yield 4 (385 mg). C, H, N, Cl calculated for C$_{23}$H$_{23}$N$_2$O$_2$Cl.1 HCl: Calculated: C: 63.01; H: 5.77; N: 6.68; Cl: 16.91. Found: C: 62.65; H: 5.87; N: 6.58; Cl: 17.02.

EXAMPLE 5

Ethyl 2-diazo-3-oxo-propanoate (5)

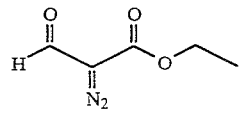

Compound 5 was synthesized according to F. M. Stojanovic, Z. Arnold, *Coll. Czech. Chem Commun,* 1967, 32, 2155–2160.

A 2M chloroform solution of (chloromethylene)-dimethylammonium chloride (12.5 mL; 0.025 mol) was treated over 15 minutes with ethyl diazoacetate (5.7 g; 0.05 mol). The temperature was held in the range between −5° C. and +10° C. and the reaction mixture was then allowed to stand at room temperature for one hour. There was evolved total 800 mL (0.036 mol) of nitrogen. The solvent was evaporated under reduced pressure, the residue treated with anhydrous ether and the resulting precipitate (4.42 g) filtered off. From the ethereal filtrate, there was isolated 54.5% of ethyl chloroacetate, b.p. 130°–136° C., n20$_D$ 1.4242. The precipitate was dissolved in 10% aqueous acetic acid and the solution allowed to stand for several hours. The oily product which separated was extracted repeatedly with ether. The ethereal extracts were combined, washed successively with a saturated solution of sodium chloride, 10% aqueous potassium hydrogen carbonate, and 10% aqueous sulfuric acid, dried over magnesium sulfate, and distilled to give 1.7 g (48%) of the ester 5, boiling at 35°–36° C./0.7 mm Hg or 82°–83° C./10 mm Hg (bath temperature; n20$_D$ 1.4792). For $C_5H_6N_2O_3$ (142.1) calculated: 42.25% C, 4.26% H, 19.71% N; found: 42.65% C, 4.42% H, 19.57% N. Ultraviolet spectrum (ethanol): $\lambda_{max}$ 217 and 249 nm (log ϵ4.24 and 4.08, resp.). Molecular weight (from the mass spectrum): 142.

EXAMPLE 6

Ethyl 2-(bromomethyl)-4-oxazolecarboxylate (6)

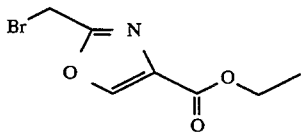

6 was synthesized according to the method of A. R. Gangloff et al., *J. Org. Chem.,* 1992, 57, 4797–4799.

To 50 mL of bromoacetonitrile was added 0.12 g of Rh$_2$(OAc)$_4$. A 50 mL bromoacetonitrile solution of 5 (2.84 g, 20 mmol) was added dropwise via syringe pump at a rate of 5 mL/hour to the stirring rhodium acetate solution which had been heated to 70° C. Once the addition was complete, the reaction was maintained at 70° C. an additional 8 hours. The excess bromoacetonitrile was removed from the reaction via distillation. The residue was filtered through a pad of silica gel which was washed with hexanes and dichloromethane. The solvent from the dichloromethane wash was removed in vacuo. The yield of compound 6 was 3.67 g (78%).

EXAMPLE 7

Ethyl 2-[(8-chlorodibenz[b,f][1,4]oxazepin-10(11H)yl)methyl]-4-oxazole carboxylate (7)

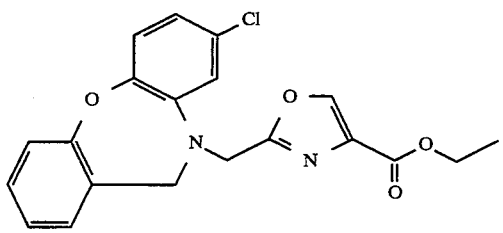

To 50 mL toluene of 8-chlorodibenz[b,f][1,4]oxazepine (1.16 g, 5 mmol) was added compound 6 (1.17 g, 5 mmol), N,N-diisopropylethylamine (1.7 mL, 10 mmol), and NaI (5 mg). The reaction was heated at reflux for 24 hours. The reaction was poured directly onto a column of silica gel and chromatographed according to Still et al., supra. The yield of compound 7 was 1.38 g (72%). Analysis Calculated for $C_{20}H_{18}N_2O_4Cl$: C: 62.42; H: 4.45; N: 7.28; Cl: 9.21. Found: C: 62.14; H: 4.42; N: 7.25; Cl: 9.10.

EXAMPLE 8

2-[(8-chlorodibenz[b,f][1,4]oxazepin-10(11H)yl)methyl]-4-oxazole carboxylic acid (8)

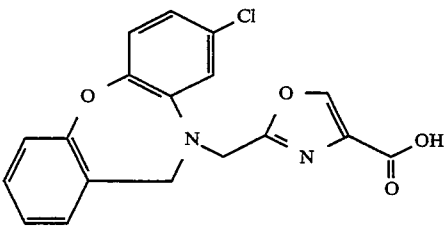

To a 10 mL MeOH:THF (1:1) stirring solution of 7 (0.56 g, 1.5 mmol) was added 4.5 mL of N NaOH. After one hour, the reaction was adjusted to pH 3. The organic solvents were removed in vacuo. A white precipitate was filtered, washed with water, and dried in a vacuum oven at 60° C. The yield of 8 was 0.48 g (89%). Analysis Calculated for $C_{18}H_{13}N_2O_4Cl$: C: 60.60; H: 3.67; N: 7.85; Cl: 9.94. Found: C: 60.56; H: 3.67; N: 7.86; Cl: 10.24.

EXAMPLE 8A

2-[(8-chlorodibenz[b,f][1,4]oxazepin-10(11H)yl)methyl]-4-oxazole carboxylic acid, sodium salt (8A)

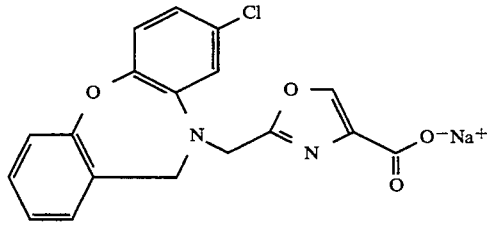

To a 2 mL water solution of 8 (0,063 g, 0.177 mmol) was added 0.177 mL of N NaOH. The solution was

EXAMPLE 9

2-[(8-chlorodibenz[b,f][1,4]oxazepin-10(11H)yl)methyl]-N-[2-(2-pyridinyl)ethyl]-4-oxazolecarboxamide, hydrochloride (9)

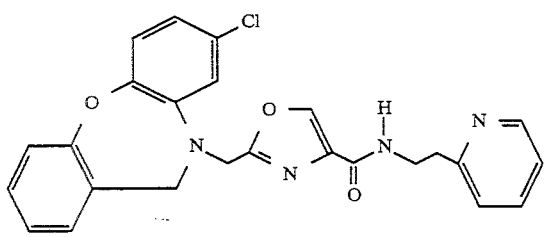

To a stirring 5 mL dimethylacetamide (DMA) solution of 8 (0.47 g, 1.3 mmol) in an ice bath was added 2-(2-ethylamino)pyridine (0.17 g, 1.6 mmol), N,N-dimethylaminopropylethylcarbodiimide hydrochloride (0.31 g, 1.6 mmol), hydroxybenzotriazole (0.22 g, 1.6 mmol), and triethylamine (0.23 mL). With warming to ambient temperature, the reaction mixture was stirred overnight. To the reaction was added 25 mL EtOAc and 25 mL H$_2$O. The organic layer was washed with 2×25 mL of H$_2$O, dried over Na$_2$SO$_4$ anhydrous, filtered, and concentrated in vacuo to yield 0.51 g (85%) of the free base. The residue was dissolved in 100 mL Et$_2$O to which was added 2 mL 6.8N HCl/dioxane. The precipitate was filtered, washed with Et$_2$O, and dried in a vacuum oven at 60° C. Analysis Calculated for C$_{25}$H$_{21}$N$_4$O$_3$Cl.1.2 HCl.0.3 H$_2$O C: 58.78; H: 4.51; N: 10.98; Cl: 14.87. Found: C: 8.50; H: 4.44; N: 10.66; Cl: 15.29.

EXAMPLE 10

2-[(8-chlorodibenz[b,f][1,4]oxazepin-10(11H)yl)methyl]-N-(2-pyridinylmethyl)-4-oxazolecarboxamide, monohydrochloride (10)

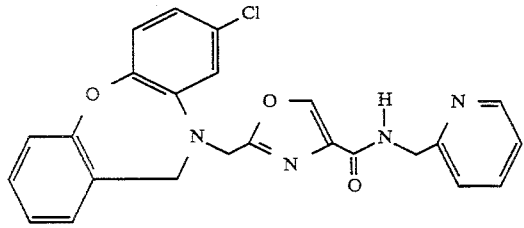

10 was prepared in the same manner as 9 using 2-aminomethylpyridine (0.073 g, 0.67 mmol). The yield of was 58%. Analysis Calculated for C$_{24}$H$_{19}$N$_4$O$_3$Cl.0.9 HCl.0.5 H$_2$O C: 58.98; H: 4.31; N: 11.46; Cl: 13.78. Found: C: 59.13; H: 4.27; N: 11.44; Cl: 13.73.

EXAMPLE 11

2-[(8-chlorodibenz[b,f][1,4]oxazepin-10(11H)yl)methyl]-N-(4-pyridinylmethyl)-4-oxazolecarboxamide, monohydrochloride (11)

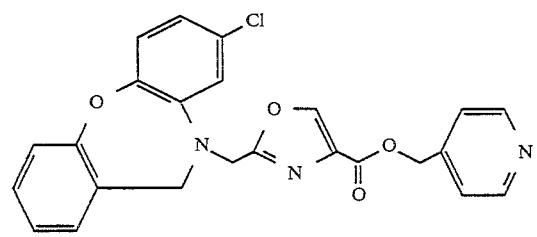

11 was prepared in the same manner as 9 starting with 0.67 mmol of 4-aminomethylpyridine to yield 0.14 g (56%). Analysis Calculated for C$_{24}$H$_{19}$N$_4$O$_3$Cl.HCl.1.5 H$_2$O C: 56.48; H: 4.54; N: 10.98; Cl: 13.89. Found: C: 56.79; H: 4.54; N: 10.70; Cl: 13.59.

EXAMPLE 12

4-pyridinylmethyl 2-[(8-chlorodibenz[b,f][1,4]oxazepin-10(11H)-yl)methyl]-4-oxazole carboxylate, hydrochloride (12)

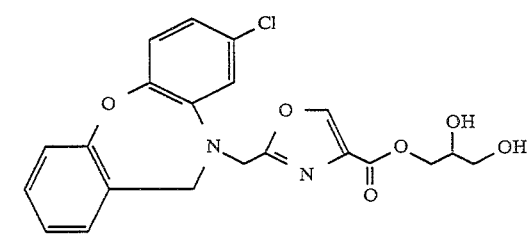

12 was prepared in the same manner as 9 starting with 4-hydroxymethylpyridine (0.45 g, 0.45 mmol). Analysis Calculated for C$_{24}$H$_{18}$N$_3$O$_4$Cl.1.6 HCl.0.4 H$_2$O C: 56.15; H: 4.00; N: 8.18; Cl: 17.95. Found: C: 55.99; H: 4.11; N: 8.07; Cl: 18.07.

EXAMPLE 13

2,3-dihydroxypropyl 2-[(8-chlorodibenz[b,f][1,4]oxazepin-10(11H)-yl)methyl]-4-oxazole carboxylate (13)

To an ice bath cooled 10 mL THF solution of 8 (0.36 g, 1 mmol) was added solketal (0.26 g, 2 mmol), triphenylphosphine (0.29 g, 1.1 mmol), and diisopropyl azodicarboxylate (0.22 g, 1.1 mmol). After stirring for 2 hours at ice bath temperature, the reaction was allowed to warm to ambient temperature and was stirred for 16 hours. The reaction mixture was chromatographed as described hereinabove. The protected product was treated with N HCl to remove the acetonide. The reaction mixture was chromatographed again to yield 13. Analysis Calculated for C$_{21}$H$_{19}$N$_{2}$O$_{6}$Cl.0.1 HCl. C: 58.05; H: 4.43; N: 6.45; Cl: 8.98. Found: C: 57.68; H: 4.38; N: 6.34; Cl: 9.08.

EXAMPLE 14

2-[(8-chlorodibenz[b,f][1,4]oxazepin-10(11H)yl)methyl]-N-[2-(4-pyridinyl)ethyl]-4-oxazolecarboxamide, hydrochloride, acetate (14)

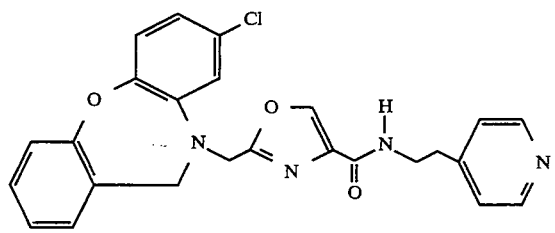

To a stirring 5 mL DCM solution of 7 (0.19 g, 0.5 mmol) was added 4-(2-aminoethyl)pyridine (0.065 g, 0.6 mmol) and trimethylaluminum (0.3 mL of 2M solution). After heating the reaction at reflux for 5 hours, the reaction mixture was added to 5 mL N NaOH. The organic layer was washed with 5 mL H$_2$O. The organic layer was dried over Na$_2$SO$_4$ anhydrous, filtered, and concentrated in vacuo. The product was chromatographed as described hereinabove. The free base was dissolved in acetic acid, treated with N HCl, and lyophilized to yield 0.06 g (26%) of 14. Analysis Calculated for C$_{25}$H$_{21}$N$_4$O$_3$Cl.1.5 HCl.1.5 H$_2$O.0.6HOAc C: 54.38; H: 4.86; N: 9.68; Cl: 15.32. Found: C: 54.78; H: 4.65; N: 9.33; Cl: 15.01.

EXAMPLE 15

2-[(8-chlorodibenz[b,f][1,4]oxazepin-10(11H)yl)methyl]-N-(2-thienylmethyl)-4-oxazolecarboxamide (15)

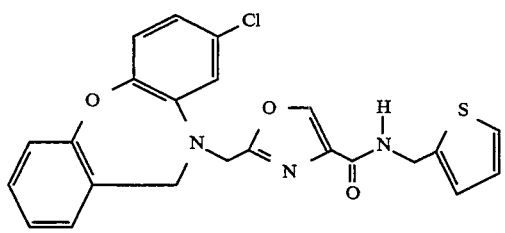

15 was prepared in the same manner as 14 starting with 2-aminomethylthiophene (0.06 g, 0.5 mmol) to yield 0.10 g (45%). Analysis Calculated for C$_{23}$H$_{18}$N$_3$O$_3$ClS. C: 60.81; H: 3.93; N: 9.10; Cl: 7.84. Found: C: 61.13; H: 4.01; N: 9.30; Cl: 8.52.

EXAMPLE 16

2-[(8-chlorodibenz[b,f][1,4]oxazepin-10(11H)yl)methyl]-N-5-pyrimidinyl-4-oxazolecarboxamide (16)

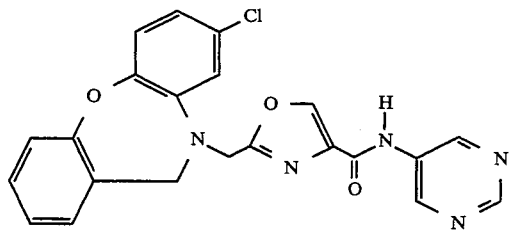

16 was prepared in the same manner as 15 starting with 5-aminopyrimidine (0.06 g, 0.5 mmol) to yield 0.19 g (86%). Analysis Calculated for C$_{22}$H$_{16}$N$_5$O$_3$Cl.0.2 H$_2$O. C: 60.40; H: 3.78; N: 16.01; Cl: 8.10. Found: C: 60.38; H: 3.85; N: 15.92; Cl: 8.20.

EXAMPLE 17

2-[(8-chlorodibenz[b,f][1,4]oxazepin-10(11H)yl)methyl]-N-4-pyridinyl-4-oxazolecarboxamide, hydrochloride (17)

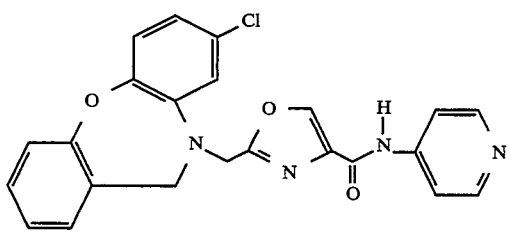

17 was prepared in the same manner as 15 starting with 4-aminopyridine (0.05 g, 0.5 mmol) to yield 0.10 g (45%). Analysis Calculated for C$_{23}$H$_{17}$N$_4$O$_3$Cl.0.6 HCl.0.2 H$_2$O. C: 60.27; H: 3.96; N: 12.22; Cl: 12.38. Found: C: 60.03; H: 3.96; N: 12.07; Cl: 12.27.

EXAMPLE 18

2-bromomethyl-4-carboxyethyl-thiazole (18)

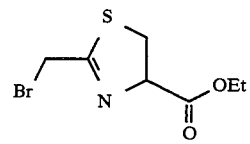

To a stirring solution of 4-carboxyethyl-2-methyl thiazole (30.3 g) in CCl$_4$ (1L) was added NBS (37.7 g) and AIBN (2.2 g). The resulting mixture was refluxed and irradiated with UV light for 4 hours. The mixture was cooled to room temperature and filtered. The solution was flash chromatographed (CH$_2$Cl$_2$) to yield 36.6 g of a red oil. This material was used without further purification.

EXAMPLE 19 ethyl 2-[(8-chlorodibenz[b,f][1,4]oxazepine-10(11H)yl)methyl]-4-thiazolecarboxylate (19)

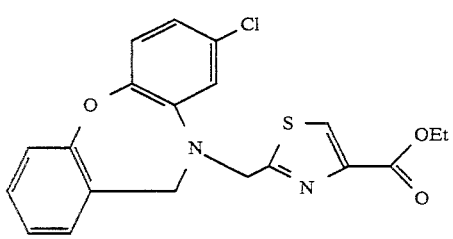

A solution of 8-chlorodibenzoxazepine (4 g) and 18 (8 g) in toluene (500 mL), diisopropylethylamine (4.5 g) and sodium iodide (500 mg) was refluxed under a N₂ atmosphere for 20 hours. The reaction mixture was allowed to cool, then chromatographed on silica gel (CH$_2$Cl$_2$) to yield 6.46 g of the crude product as a yellow solid. The product was then crystallized from ethanol to yield 19 as a white solid (3.4 g). DSC: 151.29° C. Analysis Calculated for $C_{20}H_{17}N_2O_3SCl$: C: 59.92; H: 4.27; N: 6.99; Cl: 8.84; S: 8.00. Found: C: 59.78; H: 4.29; N: 6.95; Cl: 8.78; S: 8.63.

EXAMPLE 20

2-[(8-chlorodibenz[b,f][1,4]oxazepin-10(11H)yl)methyl]-4-thiazolecarboxylic acid, sodium salt (20)

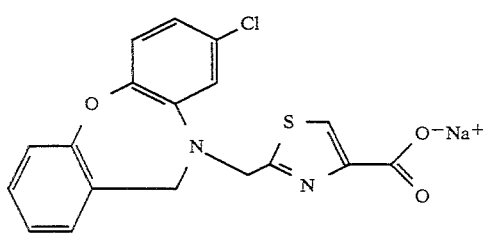

A solution of 19 (1.72 g) in THF (30 mL), MeOH (15 mL) and NaOH (1M, 13 mL) was stirred for 1 hour. The solvent was reduced under reduced pressure to yield a white precipitate, which was filtered, washed with cold water and dried under vacuum to yield 1.7 g of 20 as a white solid. Analysis Calculated for $C_{18}H_{12}N_2O_3SClNa \times 0.75$ H$_2$O: Calculated: C: 52.95; H: 3.33; N: 6.86; Cl: 8.68; S: 7.85. Found: C: 53.29; H: 3.11; N: 6.85; Cl: 8.59; S: 7.37.

EXAMPLE 21

2-[(8-chlorodibenz*b,f*][1,4]oxazepin-10(11H)yl)methyl]-N-(4-pyridinylmethyl)-4-thiazolecarboxamide, acetate, hydrochloride (21)

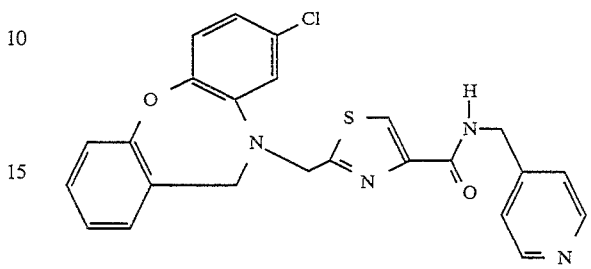

To a stirring solution of 20 (300 mg) and 4-aminomethylpyridine (92 mg) in Et$_3$N (81 mg) and DMF (5 mL) at 0° C. under N$_2$ was added HOBT (109 mg) and EDC (155 mg). The reaction was allowed to slowly warm to room temperature, and stirred for 20 hours. The solvent was removed, followed by the addition of EtOAc (400 mL) and extracted with brine (4×100 mL), and dried (Na$_2$SO$_4$) to yield 365 mg of a white solid. This material was flash chromatographed (CHCl$_3$: EtOH (95:5)) to yield 251 mg of a white solid.

This material was dissolved in HCl (1M, 6 mL) and lyophilized and relyophilized from glacial acetic acid (10 mL) to yield 275 mg of 21 as a white foam. Analysis Calculated for $C_{24}H_{19}N_4O_2SCl \times 1.66$ HCl×1 AcOH×0.33 H$_2$O: C: 52.97; H: 4.33; N: 9.50; Cl: 16.00; S: 5.44. Found: C: 52.69; H: 4.14; N: 9.45; Cl: 15.81; S: 5.78.

EXAMPLE 22

2-[(8-chlorodibenz[b,f][1,4]oxazepin-10(11H)yl)methyl]-N-(4-pyridinylmethyl)-4-thiazolecarboxamide (22)

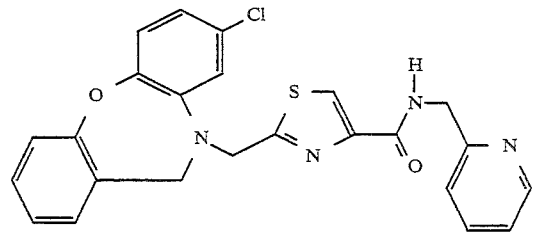

A mixture of 19 (500 mg) and 2-aminomethylpyridine (2 mL) was heated at 120° C. for 1 hour. The mixture was cooled to room temperature and flash chromatographed on silica gel (CHCl$_3$: EtOH (95:5)) to yield 380 mg of a yellow foam. Analysis Calculated for $C_{24}H_{19}N_4O_2SCl$: C: 62.26; H: 4.14; N: 12.10; Cl: 7.66. Found: C: 62.11; H: 4.52; N: 11.80; Cl: 7.65.

EXAMPLE 23

8-chloro-10,11-dihydro-10-[(2-methyl-4-thiazolyl)methyl]dibenz[b,f][1,4]oxazepine hydrochloride (23)

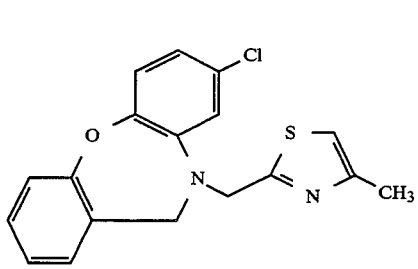

A mixture of 8-chlorodibezoxazepine (2 g), 4-chloromethyl-2-methyl thiazole hydrochloride (1.75 g), KI (1.6 g) in acetonitrile was refluxed for 16 hours. The solvent was removed under reduced pressure. The residue was taken up in EtOAC (300 mL), extracted with HCl (1M, 2×150 mL), dried (Na$_2$SO$_4$) and evaporated to yield a brown oil. This material was flash chromatographed on silicagel (CH$_2$Cl$_2$), and rechromatographed (toluene) to yield 465 mg of a brown gum. This material was dissolved in acetone and treated with HCl/dioxane to yield 23 as a yellow solid (407 mg). Analysis Calculated for C$_{18}$H$_{15}$N$_2$OSCl×1.17 HCl: C: 56.08; H: 4.23; N: 7.27; Cl: 19.96. Found: C: 55.77; H: 4.14; N: 7.20; Cl: 19.60.

EXAMPLE 24

8-Chloro-N-(methoxymethyl)dibenz[b,f][1.4]oxazepine-10(11)-carbothioamide (24)

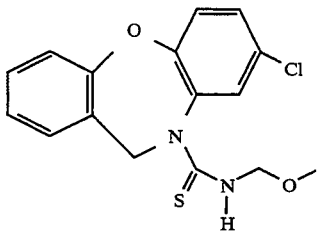

To a stirred solution of 8-chloro-dibenz[b,f][1,4]oxazepine (2.6 g) in tetrahydrofuran (50 mL) at −23° C. was added a 1.5M ether solution of methyl lithium (7.5 mL). After 1 hour, methoxymethylisothiocyanate (1.2 g) was added. After 1 hour, saturated aqueous NH$_4$Cl was added and the mixture was extracted with ethyl acetate. The organic phase was dried over MgSO$_4$ and concentrated in vacuo. The residue was triturated with ether when 24 precipitated as a pale yellow solid (2 g). This material was used in Example 25 without further purification.

EXAMPLE 25

2-(8-Chlorodibenz[b,f][1,4]oxazepin-10(11H)-yl)-4-thiazolecarboxylic acid (25)

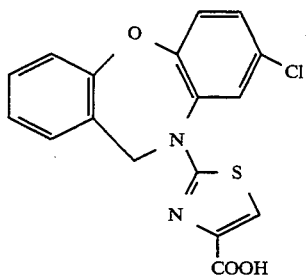

A mixture of 24 (1.13 g), ethyl bromoacetate (0.47 mL) and ethanol (15 mL) was heated to reflux. After 5 minutes, the volatiles were removed and the residue (Ethyl ester-1, General Reaction Scheme No. 2) was heated with a mixture of THF (5 mL) and 1N lithium hydroxide (15 mL) on a steam bath for 1 hour. The mixture was cooled to 10° C. and acidified with 1N HCl. The mixture was extracted with ethyl acetate. The organic extract was dried and concentrated to give 25 as a pale yellow solid. This material was used without further purification.

EXAMPLE 26

2-(8-Chlorodibenz[b,f][1,4]oxazepin-10(11H)-yl)-N-(4-pyridinylmethyl)-4-thiazolecarboxamide, monohydrochloride (26)

To a stirred solution of 25 (0.55 g) in CH$_2$Cl$_2$ (10 mL) at 0° C. was added 4-methylmorpholine (0.168 mL) and isobutyl chloroformate (0.199 mL) successively. After 30 minutes, 4-(aminomethyl)pyridine (0.156 mL) was added. The mixture was allowed to warm to ambient temperature for 16 hours. The mixture was extracted with ethyl acetate and water. The organic extract was dried over MgSO$_4$ and concentrated. The residue was purified by chromatography over silica gel using ethyl acetate as eluant to give the free base of the title compound as a white solid. Hydrochloride salt of the free bases was made either by Method-A or Method-B.

Method-A: To a solution of the free base (0.4 g) in chloroform (3 mL) was added a solution of hydrogen chloride in dioxane (7N, 1 mL). The volatiles were removed in vacuo and the residue was dried at 78° C. in vacuo (1 mm Hg) to give 25 as a white solid.

Method-B: The free base was dissolved in a minimum amount of ethanol, and excess aqueous 1N HCl was added. The resulting solution was freeze-dried. The residue was further dried in vacuo (1 mm Hg) at 78° C. Analysis Calculated for $C_{23}H_{17}ClN_4O_2S$. HCl.0.5 $H_2O$: C: 55.88; H: 3.87; N: 11.33; Cl: 14.34; S: 6.49. Found: C: 55.51, H: 3.68; N: 11.08; Cl: 14.31; S: 6.51.

EXAMPLE 27

2-(8-Chlorodibenz[b,f][1,4]Oxazepin-10(11H)-yl)-N-[2-(dimethylamino)ethyl]-4-thiazolecarboxamide, monohydrochloride (27)

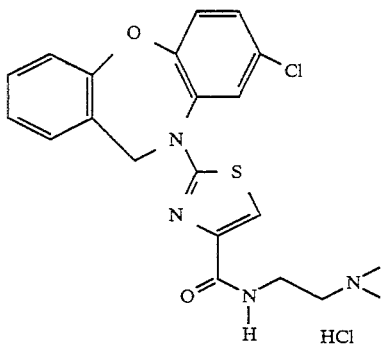

The procedure of Example 26 was repeated using N,N-dimethylethylenediamine in the place of 4-(aminomethyl)pyridine to obtain 27 as a white solid. Analysis Calculated for $C_{21}H_{21}ClN_42O_2S$. HCl. $H_2O$: C: 51.28; H: 5.00; N: 11.59; Cl: 14.67; S: 6.63. Found: C: 52.33; H: 4.70; N: 11.20; Cl: 14.46; S: 6.68.

EXAMPLE 28

2-(8-Chlorodibenz[b,f][1,4]oxazepin-10(11H)-yl)-N-4-pyridinyl-4-thiazolecarboxamide, hydrochloride (28)

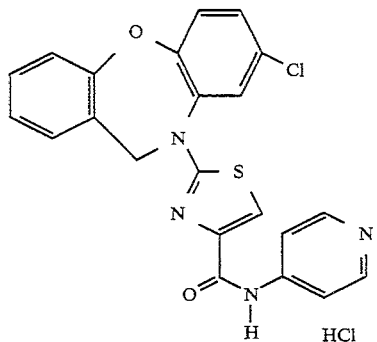

The procedure of Example 26 was repeated using 4-aminopyridine in the place of 4-(aminomethyl)pyridine to obtain 28 as a white solid. Analysis Calculated for $C_{22}H_{15}ClN_4O_2S$. 1.3 HCl. 0.9 $H_2O$: C: 53.01; H: 3.66; N: 11.24; Cl: 16.36; S: 6.43. Found: C: 53.42; H: 3.78; N: 10.66; Cl: 16.72; S: 5.89.

EXAMPLE 29

2-(8-Chlorodibenz[b,f][1,4]oxazepin-10(11H)-yl)-N-3-pyridinyl-4-thiazolecarboxamide, hydrochloride (29)

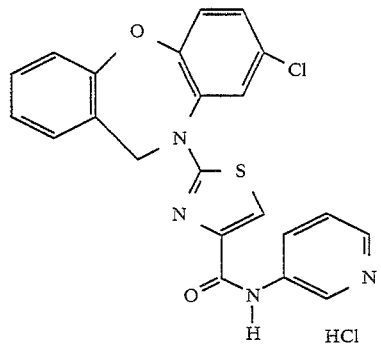

The procedure of Example 26 was repeated using 3-aminopyridine in the place of 4-(aminomethyl)pyridine to obtain 29 as a white solid. Analysis Calculated for $C_{22}H_{15}ClN_4O_2S$. 1.2 HCl. $H_2O$: C: 53.20; H: 3.69; N: 11.28; Cl: 15.70; S: 6.46. Found: C: 53.42; H: 3.45; N: 11.29; Cl: 15.92; S: 6.46.

EXAMPLE 30

2-(8-Chlorodibenz[b,f][1,4]oxazepin-10(11H)-yl)-N-2-pyridinyl-4-thiazolecarboxamide, hydrochloride (30)

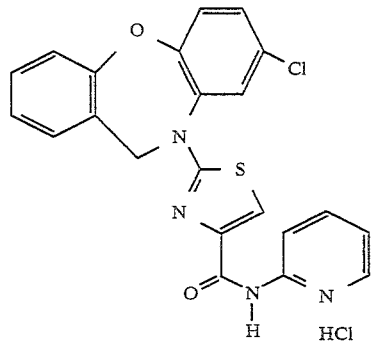

The procedure of Example 26 was repeated using 2-aminopyridine in the place of 4-(aminomethyl)pyridine to obtain 30 as a white solid. Analysis Calculated for $C_{22}H_{15}ClN_4O_2S$. 0.75 HCl. 0.5 $H_2O$: C: 56.07; H: 3.58; N: 11.89; Cl: 13.17; S: 6.80. Found: C: 53.42; H: 3.71; N: 11.43; Cl: 13.34; S: 6.78.

EXAMPLE 31

2-(8-Chlorodibenz[b,f][1,4]oxazepin-10(11H)-yl)-N-methoxy-N-methyl-4-thiazolecarboxamide (31)

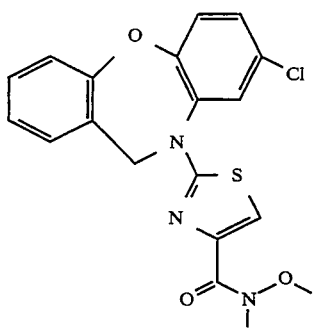

The procedure of Example 26 was repeated using N-methoxy-N-methylamine in the place of 4-(aminomethyl) pyridine to obtain 31 as a white solid.

EXAMPLE 32

1-[2-(8-Chlorodibenz[b,f][1,4]oxazepin-10(11H)-yl)-4-thiazolyl]-3-(4-pyridinyl)-1-propanone, monohydrochloride (32)

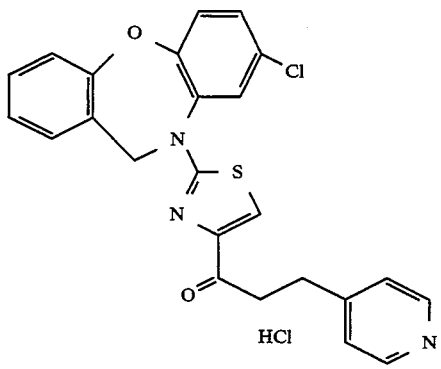

4-Ethynylpyridine was synthesized in the manner described in Tetrahedron Letters, 32(6), 757 (1991). Briefly, a mixture of trimethylsilylacetylene (25 g), 4-bromopyridine hydrochloride (25 g), bis(triphenylphosphine)palladium (II) chloride (1.1 g), copper iodide (0.4 g) and diethylamine (100 mL) was stirred at room temperature for 16 hours. The mixture was concentrated and partitioned between water and ether. The organic phase was filtered through a bed of neutral alumina. The filtrate was concentrated and stirred with methanol (150 mL) and potassium carbonate (20 g) for 10 minutes at room temperature. The mixture was filtered and the filtrate was concentrated. The residue was chromatographed on silica gel using 70% ether in hexane to give the title product as a highly colored solid. The solid was washed rapidly with ether-hexane to give 4-ethynylpyridine as a pale yellow solid.

To a stirred solution of 4-ethynylpyridine (0.21 g) in THF (10 mL) at −78° C. was added n-butyllithium (1.6M in hexane, 1.28 mL). After 30 minutes, a solution of 31 (0.7 g) in THF (3 mL) was added. The temperature was raised to 10° C. over 3 hours. Then, excess aqueous saturated NH4Cl was added and the mixture was extracted with ethyl acetate. The organic phase was dried over MgSO4 and concentrated. A solution of the residue (0.66 g) in ethyl acetate (25 mL) was shaken in a parr hydrogenator with Raney-Nickel (0.5 g) under 5 psi hydrogen atmosphere at ambient temperature for 0.95 hours. The mixture was filtered to remove the catalyst and the filtrate was concentrated. The residue was purified by chromatography using 2% methanol in ethyl acetate to give the free base of 32 as a white solid. To a solution of this solid (0.4 g) in chloroform (3 mL) was added a solution of hydrogen chloride in dioxane (7N, 1 mL). The volatiles were removed in vacuo and the residue was dried at 78° C. in vacuo (1 mm Hg) to give 32 as a white solid. Analysis Calculated for $C_{24}H18ClN_3O_2S \cdot HCl \cdot 0.5 H_2O$: C: 58.42; H: 4.09; N: 8.52; Cl: 14.37; S: 6.50. Found: C: 58.30; H: 3.95; N: 8.39; Cl: 14.21; S: 6.25.

EXAMPLE 33

Compound A 2-(8-Chlorodibenz[b,f][1,4]oxazepin-10(11H)-yl)-4-thiazolemethanol (33, Compound A)

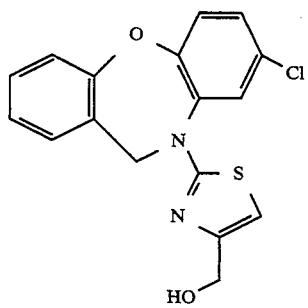

Compound B 2-(8-Chlorodibenz[b,f][1,4]oxazepin-10(11H)-yl)-a-[(4-pyridinyl)ethynyl]-4-thiazolemethanol (33, Compound B)

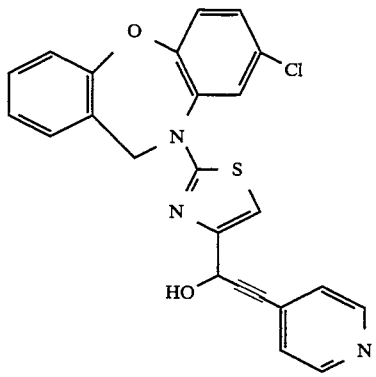

To a stirred solution of the ethyl ester of 25 (Ethyl ester-1, General Reaction Scheme No. 2, 5.5 g) in toluene (200 mL) at −78° C. was added diisobutyl aluminum hydride (1M solution in toluene, 14.21 mL). After 15 minutes, excess saturated aqueous NH4Cl was added. The cooling bath was removed. Then, 200 mL of 2N HCl was added. The layers were separated. The aqueous phase was extracted with ethyl acetate. The combined organic extract was washed with a brine solution and concentrated. The residue was chromatographed over silica gel to give first a mixture of the starting ester with an aldehyde (3.5 g, ester:aldehyde, 0.9:1) and then 33, Compound A (1 g) as colorless thick gums. This mixture of ester and aldehyde (3.3 g) in THF (5 mL) was added to a stirred THF (30 mL) solution of lithiated 4-ethynyl pyridine (prepared as for 32 from 0.6 g of 4-ethynylpyridine and 4 mL of 1M n-butyllithium in hexane) at −78° C. After 30 minutes, the reaction was worked up as for 32. The crude product was chromatographed using 60% ethyl acetate in hexane. Appropriate fractions were pooled to give 33, Compound B as a colorless white solid (1.5 g).

EXAMPLE 34

Compound A 2-(8-Chlorodibenz[b,f][1,4]oxazepin-10(11H)-yl)-a-[2Z(4-pyridinyl)ethenyl]-4-thiazolemethanol, hydrochloride (34, Compound A)

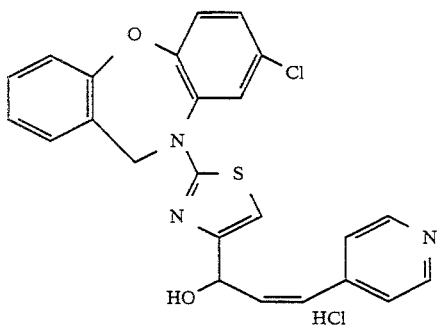

Compound B

α-[2-(8-Chlorodibenz[b,f][1,4]oxazepin-10(11H)-yl)-4-thiazolyl]-4-pyridinepropanol, dihydrochloride (34, Compound B).

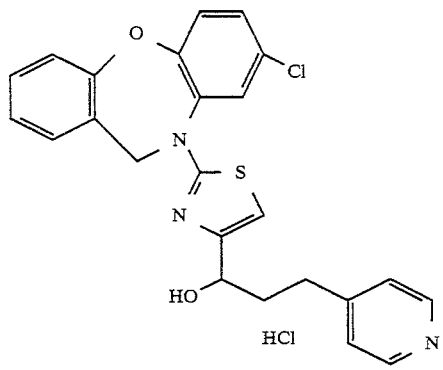

A solution of 33, Compound B (1 g) in THF (30 mL) was shaken in a parr hydrogenator with Raney-Nickel (0.5 g) under a 5 psi hydrogen atmosphere at ambient temperature for 1 hour. The mixture was filtered to remove the catalyst and the filtrate was concentrated. The catalyst was filtered off and the filtrate concentrated in vacuo. The residue was chromatographed using 80% ethyl acetate in hexane to give the free base of 34, Compound A (0.4 g) as a white solid. Continuation of the chromatography using 5% methanol in ethyl acetate gave the free base of 34, Compound B (0.13 g) as a white solid. The HCl salts of the free bases, made as described in Example 26, gave pale reddish aqueous solutions.

Compound A

Analysis Calculated for $C_{24}H_{18}ClN_3O_2S$. 1.5 HCl. 0.5 $H_2O$: C: 56.34; H: 4.04; N: 8.21; Cl: 17.32; S: 6.27. Found: C: 56.00; H: 4.07; N: 8.09; Cl: 17.58; S: 6.29.

Compound B

Analysis Calculated for $C_{24}H_{20}ClN_3O_2S$. 2.0 HCl. 0.5 $H_2O$: C: 54.20; H: 4.36; N: 7.90; Cl: 20.00; S: 6.03. Found: C: 54.48; H: 4.40; N: 7.85; Cl: 19.28; S: 6.00.

EXAMPLE 35

2-(8-Chlorodibenz[b,f][1,4]oxazepin-10(11H)-yl)-4-thiazolemethanamine (35)

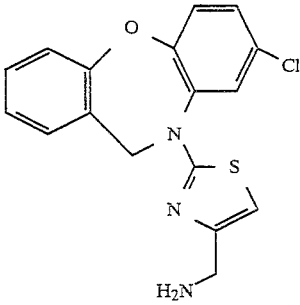

To a stirred mixture of 33, Compound A (1 g) and triphenylphosphine (0.76 g) in THF (30 mL) at −78° C. was added diethylazodicarboxylate (0.457 mL) and diphenoxyphosphorylazide (0.625 mL). The mixture was allowed to stir at ambient temperature for 20 hours. Then, the mixture was concentrated and the residue was chromatographed on silica gel. Elution using 10% ethyl acetate in hexane and combining appropriate fractions gave 1 g of a reddish liquid. This material was taken up in ether (30 mL) and the solution was cooled to −78° C. To this stirred solution was added lithium aluminum hydride (15 mL of 1M solution in THF). After 1 hour the cooling bath was removed and lithium aluminum hydride (3 mL of 1M solution in THF) was added. The mixture was allowed to stir at ambient temperature for 1 hour and then cooled to −78° C. To this was added in succession water (0.29 mL), 15% aqueous NaOH (0.29 mL) and water (0.9 mL) with 20 minute intervals. After stirring for an additional 20 minutes, the mixture was filtered through a short column of $Na_2SO_4$. The filtrate was concentrated and the residue was chromatographed using ethyl acetate containing 10% each of methanol and triethylamine. Appropriate fractions were pooled to give 35 (0.25 g) as a colorless thick liquid.

EXAMPLE 36

N-[[2-(8-Chlorodibenz[b,f][1,4]oxazepin-10(11H)-yl)-4-thiazolyl]methyl]-4-pyridinecarboxamide, hydrochloride (36)

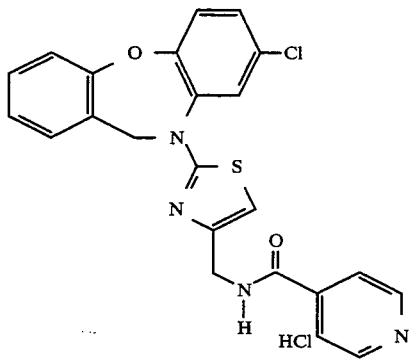

To a stirred solution of 35 (0.22 g) in CH$_2$Cl$_2$(5 mL) was added pyridine (4 mL), isonicotinoyl chloride (120 mg) and triethylamine (2 mL). The mixture was stirred at ambient temperature for 48 hours. The volatiles were removed and the residue was extracted with ethyl acetate and water. The organic extract was washed with saturated NaHCO$_3$, dried over MgSO$_4$ and concentrated. The residue was chromatographed over silica gel using ethyl acetate as eluant. Appropriate fractions were pooled to give the free base of 36 as a white solid (0.15 g). The HCl salt of the free base was made as described in Example 26 to give 36 as a white solid. Analysis Calculated for C$_{23}$H$_{17}$ClN$_4$O$_2$S. 1.5 HCl. 1 H$_2$O: C: 52.96; H: 3.96; N: 10.74; Cl: 16.99; S: 6.15. Found: C: 52.89; H: 3.99; N: 10.26; Cl: 16.62; S: 6.08.

EXAMPLE 37

2-(8-Chlorodibenz[b,f][1,4]oxazepin-10(11H)-yl)-N-(3-pyridinylmethyl)-4-thiazolecarboxamide, hydrochloride (37)

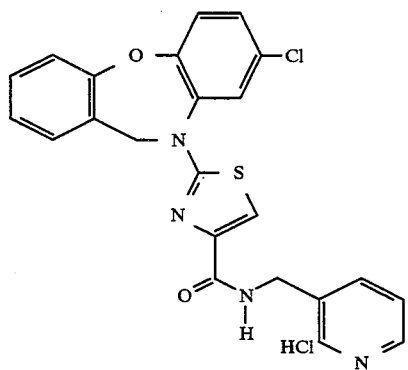

The procedure of Example 26 was repeated using 3-(aminomethyl)pyridine in the place of 4-(aminomethyl) pyridine to obtain 37 as a white solid.

Analysis Calculated for C$_{23}$H$_{17}$ClN$_4$O$_2$S. 1.4 HCl. 1 H$_2$O: C: 53.33; H: 3.97; N: 10.82; Cl: 16.43; S: 6.19. Found: C: 53.32; H: 3.90; N: 10.73; Cl: 16.29; S: 6.14.

EXAMPLE 38

1-[(Benzyloxy)methyl]-2,4,5-tribromoimidazole (38)

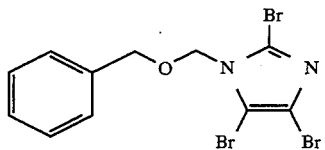

Tribromoimidazole (2.0 g, 6.6 mmol) in 25 mL of DMF solution was treated with powdered K$_2$CO$_3$ (12.7 g, 91.6 mmol). To the vigorously stirring suspension was added dropwise benzyl chloromethyl ether (1.4 g, 9.2 mmol). After 18 hours, the reaction mixture was filtered. The filtrate was concentrated in vacuo. The residue was chromatographed as described previously. The product was used immediately in Example 39.

EXAMPLE 39

1-[(Benzyloxy)methyl]-4,5-dibromoimidazole-2-carboxaldehyde (39)

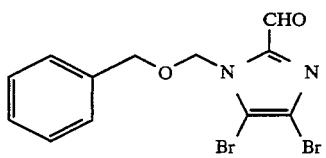

To a stirring solution of 38 (1.0 g, 2.4 mmol) in 15 mL of THF cooled to −78° C. was added n-BuLi (1.58 mL, 1.6M solution). After 1 hour, DMF (1.2 mL) was added to the reaction. After stirring for 15 minutes, the icebath was removed and the reaction was warmed to ambient temperature and then quenched with 15 mL of saturated NH$_4$Cl solution. The aqueous layer was extracted with 3×60 mL of EtOAc. The combined organic layers were dried over anhydrous Na$_2$SO$_4$, filtered, and concentrated in vacuo. The residue was chromatographed as described before. The product was used immediately in Example 40.

EXAMPLE 40

1-[(Benzyloxy)methyl]-2-hydroxymethyl-4,5-dibromoimidazole (40)

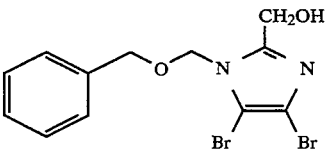

A solution of 39 (0.68 g, 1.8 mmol) and NaBH$_4$ (0.08 g, 2 mmol) in 50 mL of EtOH was allowed to stand at ambient temperature for 1.25 hours. The excess reagent was destroyed by the addition of acetic acid. The solution was stripped. The residue was dissolved in 30 mL of H$_2$O and extracted with 3×50 mL of Et$_2$O. The organic layer was washed with 1×30 mL of brine, dried, filtered and stripped. The product was used immediately in Example 41.

EXAMPLE 41

1-[(Benzyloxy)methyl]-2-bromomethyl-4,5-dibromoimidazole (41)

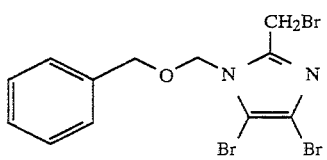

To a stirring solution of 40 (2.17 g, 5.8 mmol) and pyridine (0.06 g, 0.72 mmol) in 35 mL of Et$_2$O cooled to −65° C. was added dropwise PBr$_3$ (0.57 g, 2.1 mmol). After stirring for a total of 4 hours with gradual warming to room temperature, 50 mL of EtOAc was added to the solution. The organic layer was washed with 2×50 mL KHSO$_4$ and 1×100 mL of brine. The organic layer was dried, filtered and stripped. The product was used immediately in Example 42.

EXAMPLE 42

2-[(8-chlorodibenz[b,f][1,4]oxazepin-10(11H)yl)methyl]-1-[(benzyloxy)methyl]-4,5-dibromoimidazole (42)

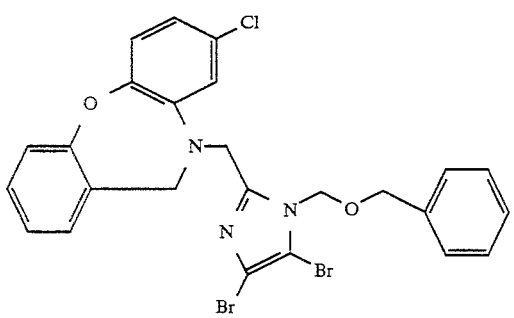

42 was prepared in the same manner as Example 7, with the exception that 41 was used instead of 6.

EXAMPLE 43

2-[(8-chlorodibenz[b,f][1,4]oxazepin-10(11H)yl)methyl]-1-[(benzyloxy)methyl]-4-bromoimidazole (43)

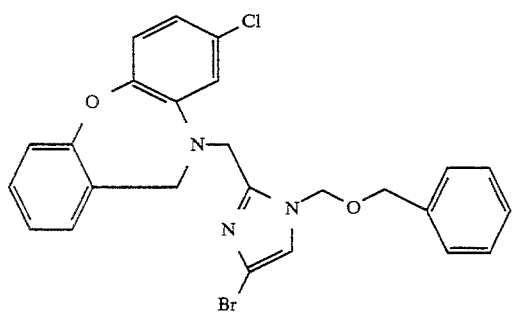

To a stirring solution of 42 (0.45 g, 0.76 mmol) in 10 mL of THF at −78° C. was added dropwise n-BuLi (0.53 mL, 1.6M solution). After 1 hour, 2-propanol (0.07 mL, 0.8 mmol) was added. After gradual warming to room temperature over 1 hour, a saturated solution of NH$_4$Cl (15 mL) was added. The reaction was extracted with 3×25 mL of EtOAc. The organic layer was dried, filtered and stripped. The product was used immediately in Example 44.

EXAMPLE 44

2-[(8-chlorodibenz[b,f][1,4]oxazepin-10(11H)yl)methyl]-1-[(phenylmethoxy)methyl]-4(1H)imidazolecarboxylic acid (44)

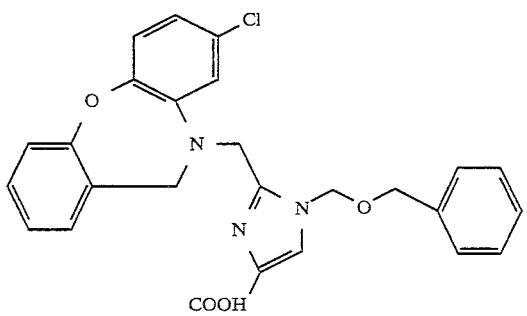

43 (10 mmol) in THF is treated with magnesium. When the Grignard reagent is formed, CO$_2$ is bubbled through the reaction. The reaction is treated with 1N HCl and is extracted with EtOAc. The organic layer is dried, filtered and stripped. The product is used immediately in Example 45.

EXAMPLE 45

8-chloro-10(11H)-[[2-(2-phenylethyl)-4-thiazolyl]carbonyl]-dibenz[b,f][1,4]oxazepine (45)

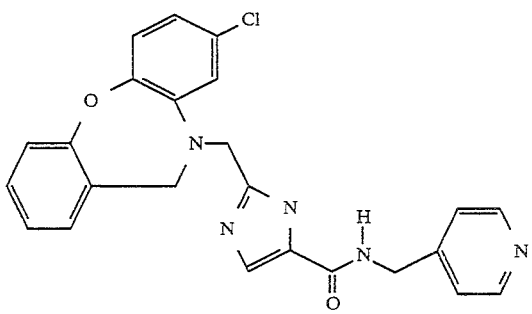

To a stirring 5 mL dimethylacetamide (DMA) solution of 44 (10 mmol) in an ice bath is added 2-(2-ethylamino)pyridine, N,N-dimethylaminopropylethylcarbodiimide hydrochloride, hydroxybenzotriazole, and triethylamine. With warming to ambient temperature, the reaction mixture is stirred over night. To the reaction is added 25 mL of EtOAc and 25 mL of H$_2$O. The organic layer is washed with 2×25 mL of H$_2$O, is dried over Na$_2$SO$_4$ anhydrous, is filtered, and is concentrated in vacuo to yield the free base. The residue is dissolved in 100 mL of Et$_2$O to which is added 2 mL of 6.8N HCl/dioxane to give the hydrochloride salt of 45.

EXAMPLE 46

8-chloro-10(11H)-[(2-methyl-4-thiazolyl)carbonyl]-dibenz[b,f][1,4]oxazepine (46)

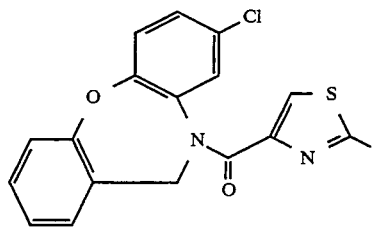

To a stirring solution of 8-chlorodibenz[b,f][1,4]oxazepine (2.0 g, 8.63 mmol) and 18 (8.6 mmol) in toluene (200 mL) at room temperature, was added $Me_3Al$ (7 mL, 14 mmol). The resulting solution was then heated to reflux for 16 hours. To the reaction was added MeOH (15 mL), and then it was poured onto 300 mL of EtOAc. The organic layer was extracted with NaOH (1M, 3×200 mL) and brine (2×200 mL). The organic layer was dried over $Na_2SO_4$ anhydrous, filtered, and concentrated in vacuo. The product was chromatographed as described previously.

Analysis calculated for $C_{18}H_{13}N_2O_2ClS$: C: 60.59; H: 3.67; N: 7.85; Cl: 9.84; S: 8.99. Found: C: 60.44; H: 3.80; N: 7.83; Cl: 9.66; S: 9.19.

EXAMPLE 47

8-chloro-10(11H)-[[2-(2-phenylethyl)-4-thiazolyl]carbonyl]dibenz[b,f][1,4]oxazepine (47)

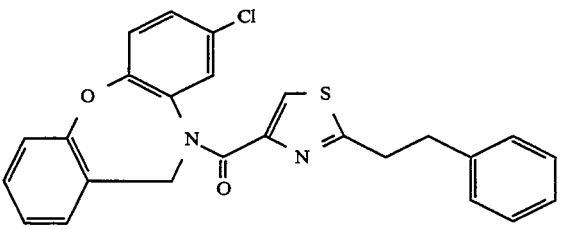

L-Cysteine ethyl ester hydrochloride (14.11 g, 76 mmol) was added to a stirring solution of hydrocinamaldehyde (10 g, 74.5 mmol) in toluene (100 mL) and $Et_3N$ (8.1 g, 80 mmol). The resulting mixture was stirred at ambient temperature overnight. The reaction mixture was filtered and washed with toluene. The solvent was removed in vacuo. The resulting thiazolidine was oxidized with $MnO_2$ (90%, battery grade).

The resulting thiazole is attached to the dibenzoxazepine as described in Example 46.

The foregoing examples are provided to enable one of ordinary skill in the art to practice the present invention. These examples are merely illustrative, however, and should not be read as limiting the scope of the invention as it is claimed in the appended claims.

(7) The Writhing Assay

The Writhing Assay is one of the most widely-used experimental procedures for measuring the analgesic activity of different narcotic and nonnarcotic analgesic agents, and involves the continuous, chemically-induced pain of visceral origin to an animal, such as a mouse or rat. [Gyires et al., *Arch. int. Pharmacodyn*, 267, 131–140 (1984); C. Vander Wende et al., *Fed. Proc.*, 15, 494 (1956); Koster et al., *Fed. Proc.*, 18, 412 (1959); and Witken et al., *J. Pharmacol. exp. Ther.*, 133, 400–408 (1961).] Chemicals which may be used to induce this pain include phenylbenzoquinone (PBQ) and acetic acid. As a result of the chemical irritation to the animal, a characteristic stretching and writhing of the animal (dorsiflexion of the animal's back, extension of its hindlimbs and the strong contraction of its abdominal musculature) will generally occur. The intensity of this pain reaction is determined by the number of writhes exhibited by the animal during a given period of time. Drugs which reduce the number of writhes of the animal appear to restore the normal nociceptive threshold of the animal.

Compounds of the present invention exhibit analgesic activity in mice, as shown by the results of the Writhing Assay presented in Table 1 below.

Charles River male albino mice, weighing 20 to 30 grams were used in this assay.

Twenty-five minutes after intragastric administration to nine or ten mice of 30 mg per kilogram of body weight of a compound of the present invention ("test compound"), 0.1 mg per 10 g of body weight of a 0.025% w/v solution of PBQ was injected intraperitoneally into each mouse. Ten mice which were given saline in place of a test compound of the invention were used as a control group.

Five minutes later, each mouse was individually placed into a glass beaker for observation, and the number of writhes occurring during the following ten-minute period was counted.

A test compound was considered to have produced analgesia in a mouse if, in accordance with the conditions set forth above, and under the test criteria employed for this assay, after the administration of 30 mg per kilogram of body weight of a compound of the present invention to the mouse, the number of writhes elicited by a mouse injected with PBQ was equal to, or less than, one-half the median number of writhes recorded for the saline-treated control group of mice that day, as described by Taber in "Predictive Value of Analgesic Assays in Mice and Rats," *Advances in Biochemical Psychopharmacology*, 8, 191 (1974).

The results for the particular compounds of the present invention analyzed in this assay, and discussed in the examples identified below which correspond thereto, are presented in Table 1 hereinbelow as fractions under the heading "WRITHING ASSAY." The fractions indicate the number of mice out of nine or ten in which a test compound produced analgesia.

The standard initial screening dose of a test compound employed in this assay was 30 milligrams per gram of body weight. If this initial screening dose of the test compound produced analgesia in seven of nine or ten mice, then the effect of additional doses of the test compound on the writhing response was evaluated, and then the $ED_{50}$ dose was generally calculated. (The slopes of the dose-response curves for all test compounds analyzed were compared as described by Tallarida and Murray, *Manual of Pharmacologic Calculations*, Page 11 (Springer Verlag, New York, 1981)).

All $ED_{50}$ doses calculated are also presented below as whole numbers in Table 1, under the heading "WRITHING ASSAY."

(b) Prostaglandin (PGE) Antagonism Assay

In order to determine the effectiveness of several of the compounds of the present invention ("test compounds") as prostaglandin $E_2$ antagonists, a prostaglandin antagonism assay was conducted, as described below, to determine the ability of these compounds to inhibit prostaglandin $E_2$-induced contractions of segments of guinea pig ileum. If a test compound inhibits prostaglandin $E_2$-induced contractions, it suggests that the compound functionally antagonizes prostaglandin $E_2$.

Male albino guinea pigs weighing 200 to 500 grams were sacrificed by cervical dislocation. The ilea were then quickly removed from the guinea pigs and placed in a modified Tyrode solution, a solution which is known to those skilled in the art, containing one-half of the usual amount of magnesium ions.

Segments of ileum about 2 cm long were then cut and mounted in a 10-mL tissue bath containing the modified Tyrode solution. The solution was maintained at 37° C. and aerated with a gaseous mixture of 95% oxygen and 5% carbon dioxide. Data for a control prostaglandin $E_2$ dose response curve plotting concentration of prostaglandin $E_2$ versus the intensity of contractions, detected isotonically, was then obtained by experimentally adjusting the dose of the prostaglandin $E_2$ being injected into the tissue bath, in a manner known by those of skill in the art.

Solutions or suspensions containing an initial concentration (3 micromolar) of a test compound in modified Tyrode solution ("test solutions/suspensions") were then separately substituted for the control bath solution. Each test solution/suspension was then kept in constant contact with the ileum tissue, except for brief periods to drain the bath in preparation for rinsing with fresh test solution/suspension. A second prostaglandin $E_2$ dose response curve was then generated for prostaglandin $E_2$ in the presence of a test compound.

A dose ratio of $EC_{50}$ doses was then calculated from the results of each test in a manner known by those of skill in the art. A test compound was determined to be "active" if the initial concentration used yielded at least a two-fold shift (dose ratio greater than or equal to 2) in the dose response curve for prostaglandin $E_2$. An estimated $pA_2$ value (a statistical constant which is a common measure of expressing the potency of a particular drug as an antagonist) was reported for "active" compounds under the assumption that the slope of the Schild plot does not deviate significantly from $-1.0$. If the initial concentration of test compound yielded at least a five-fold shift (dose ratio greater than or equal to 5) in the dose response curve for prostaglandin $E_2$, then varying concentrations of the test compound were assayed, and a $pA_2$ value for that compound was calculated by Schild plot calculations, as described by H. O. Schild, "pA, A New Scale for the Measurement of Drug Antagonism," Br. J. Pharmacol, 2, 189 (1947). The higher the value calculated for the pA2, the more potent a particular compound is as a prostaglandin $E_2$ antagonist.

The results of this prostaglandin antagonism assay are also presented in Table 1 below. The compounds of the present invention which were tested in this assay, and for which results are presented in Table 1, correspond to the particular examples specified in Table 1.

TABLE 1

| | Data Generated from the Assays | |
|---|---|---|
| Example Number | WRITHING ASSAY (number/9 or 10 or $ED_{50}$) Intragastric | PGE ANTAGONISM IN GUINEA PIG ILEUM ($pA_2$) |
| Example 7 | 9/10 | 6.1 |
| Example 8A | 1/10 | 7.4 |
| Example 9 | 7/10 | 6.7 |
| Example 10 | 2/10 | 7.5 |
| Example 11 | 9/10 | 7.6 |
| Example 12 | 4/10 | * |
| Example 14 | 6/10 | 7.8 |
| Example 15 | 7/10 | 6.8 |
| Example 16 | * | 5.5 |
| Example 17 | * | 6.4 |
| Example 19 | 1/10 | 5.8 |
| Example 20 | 5/10 | 8.1 |
| Example 21 | 7/10 | 6.1 |
| Example 23 | 1/9 | * |
| Example 26 | 9.77 | 6.1 |
| Example 27 | 6/10 | * |
| Example 28 | 10/10 | 5.5 |
| Example 29 | 6/10 | 6.0 |
| Example 30 | 4/10 | * |
| Example 32 | 6/10 | 6.2 |
| Example 34A | 9.7 | 6.1 |
| Example 34B | 5/10 | 5.8 |
| Example 36 | 6/10 | 6.2 |
| Example 37 | 1/10 | 6.0 |

* - Not tested.

While the present invention has been described herein with some specificity, and with reference to certain preferred embodiments thereof, those of ordinary skill in the art will recognize numerous variations, modifications and substitutions of that which has been described which can be made, and which are within the scope and spirit of the invention. For example, effective dosages other than the preferred ranges set forth hereinabove may be applicable as a consequence of variations in the responsiveness of the animal being treated, dosage-related adverse effects, if any, and analogous considerations. Likewise, the specific pharmacological responses observed may vary according to, and depending upon, the particular active compound selected, or whether there are present certain pharmaceutical carriers, as well as the type of formulation and mode of administration employed. Such expected variations and/or differences in the results are contemplated in accordance with the objects and practices of the present invention. It is intended therefore that all of these modifications and variations be within the scope of the present invention as described and claimed herein, and that the invention be limited only by the scope of the claims which follow, and that such claims be interpreted as broadly as is reasonable.

What is claimed is:

1. A compound having the structure:

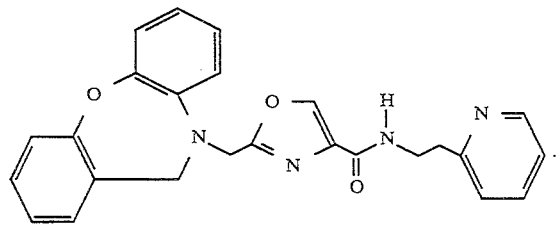

2. A compound having the structure:
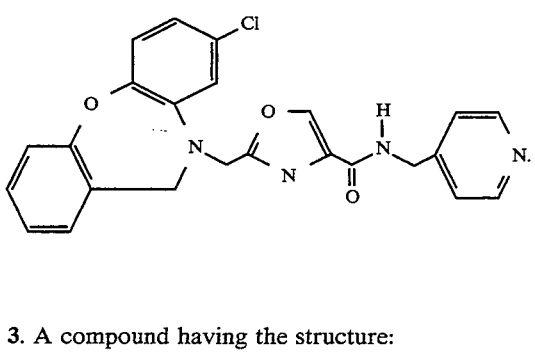
3. A compound having the structure:
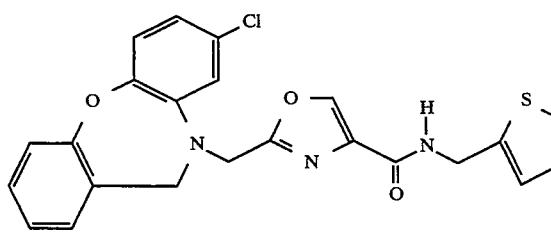
4. A compound having the structure:
5. A compound having the structure:
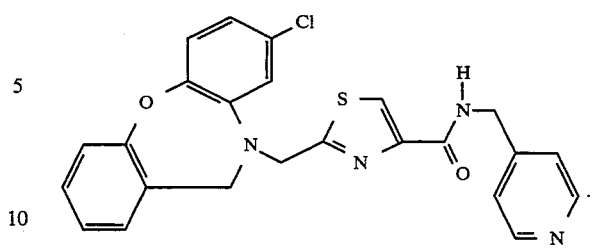
5. A compound having the structure:
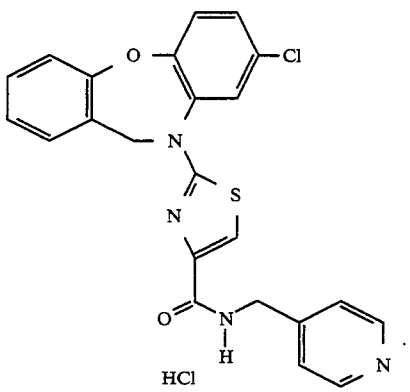
6. A compound having the structure:
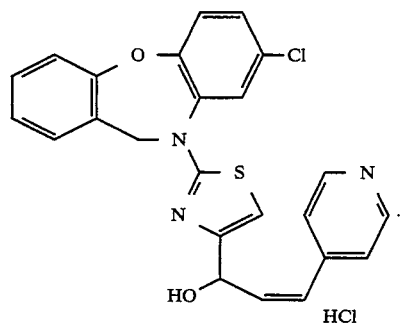
* * * * *